US012781176B2

(12) United States Patent
Murthy

(10) Patent No.: US 12,781,176 B2
(45) Date of Patent: Nov. 3, 2026

(54) CELL CULTURE SYSTEMS AND USES THEREOF

(71) Applicant: FLASKWORKS, LLC, Boston, MA (US)

(72) Inventor: Shashi K. Murthy, Newton, MA (US)

(73) Assignee: FLASKWORKS, LLC, Boston, MA (US)

( * ) Notice: Subject to any disclaimer, the term of this patent is extended or adjusted under 35 U.S.C. 154(b) by 1236 days.

(21) Appl. No.: 17/601,060

(22) PCT Filed: Apr. 2, 2020

(86) PCT No.: PCT/US2020/026386
§ 371 (c)(1),
(2) Date: Oct. 2, 2021

(87) PCT Pub. No.: WO2020/206121
PCT Pub. Date: Oct. 8, 2020

(65) Prior Publication Data

US 2022/0169972 A1 Jun. 2, 2022

Related U.S. Application Data

(60) Provisional application No. 62/828,696, filed on Apr. 3, 2019.

(51) Int. Cl.
*C12M 1/36* (2006.01)
*C12M 1/00* (2006.01)

(52) U.S. Cl.
CPC ............ *C12M 41/48* (2013.01); *C12M 23/28* (2013.01)

(58) Field of Classification Search
CPC ...... C12M 41/48; C12M 23/28; C12M 41/12; C12M 41/26; C12M 41/34
See application file for complete search history.

(56) References Cited

U.S. PATENT DOCUMENTS

| | | | |
|---|---|---|---|
| 8,639,043 | B2 | 1/2014 | Levenson et al. |
| 2005/0158701 | A1 | 7/2005 | West |
| 2006/0019385 | A1 | 1/2006 | Smith et al. |
| 2008/0032398 | A1 | 2/2008 | Cannon et al. |
| 2013/0004938 | A1 | 1/2013 | Alexandrov et al. |
| 2013/0095566 | A1 | 4/2013 | Oltvai et al. |
| 2016/0145563 | A1 | 5/2016 | Berteau et al. |
| 2016/0174902 | A1 | 6/2016 | Georgescu et al. |
| 2017/0053398 | A1 | 2/2017 | Mahoor et al. |
| 2018/0231966 | A1 | 8/2018 | Selker et al. |

FOREIGN PATENT DOCUMENTS

| | | | | |
|---|---|---|---|---|
| CN | 109401961 | A * | 3/2019 | ............ C12M 41/48 |
| DE | 202014102506 | U1 | 6/2014 | |
| EP | 2484750 | A1 | 8/2012 | |
| EP | 2995676 | A1 | 3/2016 | |
| JP | 2006-55027 | A | 3/2006 | |
| JP | 2010-104299 | A | 5/2010 | |
| WO | 2011/005773 | A2 | 1/2011 | |
| WO | 2016/182551 | A1 | 11/2016 | |
| WO | WO-2018005521 | A2 * | 1/2018 | ............ C12M 23/24 |
| WO | 2018/041423 | A1 | 3/2018 | |
| WO | 2020/206121 | A2 | 10/2020 | |

OTHER PUBLICATIONS

Shukla, A. A. and Gottschalk, U. Single-use disposable technologies for biopharmaceutical manufacturing. Trends in Biotechnology 31(3) 147-154 (2013). DOI: 10.1016/j.tibtech.2012.10.004. (Year: 2013).*

Hyun Im, S. Kim K. R., Park, Y. M. et al. An animal cell culture monitoring system using a smartphone-mountable paper-based analytical device. Sensors and Actuators B: Chemical 229, 166-173 (2016). DOI: 10.1016/j.snb.2016.01.121. (Year: 2016).*

Amirkia, V. and Qiubao, P. Cell-culture Database: Literature-based reference tool for human and mammalian experimentally based cell culture applications. Bioinformation 8(5), 237-8 (2012). DOI: 10.6026/97320630008237. (Year: 2012).*

Konagaya, S., Ando, T., Yamauchi, T. et al. Long-term maintenance of human induced pluripotent stem cells by automated cell culture system. Sci Rep 5, 16647 (2015). DOI: 10.1038/srep16647. (Year: 2015).*

Franscini, N., Wuertz, K., Patocchi-Tenzer, I., et al. Development of a novel automated cell isolation, expansion, and characterization platform. J Lab Autom 6(3), 204-13 (2011). DOI: 10.1016/j.jala.2011.01.002. (Year: 2011).*

Mehrotra, S., Prakash, O., Mishra, B.N. et al. Efficiency of neural networks for prediction of in vitro culture conditions and inoculum properties for optimum productivity. Plant Cell Tiss Organ Cult. 95: 29-35 (2008). DOI: https://doi.org/10.1007/s11240-008-9410-0 (Year: 2008).*

Sewsynker-Sukai, Y., Faloye F., and Kana, E.B.G. Artificial neural networks: an efficient tool for modelling and optimization of biofuel production (a mini review). Biotechnology & Biotechnological Equipment. 31(2): 221-235 (2017). DOI: https://doi.org/10.1080/13102818.2016.1269616. (Year: 2017).*

(Continued)

*Primary Examiner* — Lori A. Clow
*Assistant Examiner* — Diana P Sanford
(74) *Attorney, Agent, or Firm* — Brown Rudnick LLP; Adam M. Schoen

(57) ABSTRACT

Systems for monitoring and controlling cell culture comprise a cell culture apparatus operably associated with a controller. The controller comprises a hardware processor coupled to memory containing instructions executable by the processor to cause the controller to receive data associated with cells to be cultured; connect to one or more databases to receive cell culture protocol data; and determine a cell culture protocol for the cells to be cultured. Methods of determining a cell culture protocol comprise receiving data associated with cells to be cultured; connecting to one or more databases to receive data about cell culture protocols; and determining a cell culture protocol for the cells to be cultured.

22 Claims, 14 Drawing Sheets

(56) References Cited

OTHER PUBLICATIONS

Amirkia, 2012, Cell-culture Database: Literature-based reference tool for human and mammalian experimentallybased cell culture applications, Bioinformation, 8(5):237-238.
Ben-Hur, 2001, Support Vector Clustering, J Mach Learning Res, 2:125-137.
Breiman, 2001, Random Forests, Machine Learning, 45:5-32.
Chen, 2016, XGBoost: A Scalable Tree Boosting System, In Proceedings of the 22nd ACM SIGKDD International Conference on Knowledge Discovery and Data Mining, Association for Computing Machinery, 785-794.
Criminisi, 2012, Decision Forests: A unified framework for classification, regression, density estimation, manifold earning and semi-supervised learning, Foundations and Trends in Computer Graphics and Vision, 7(2-3):81-227.
Dieterle, 2006, Probabilistic quotient normalization as robust method to account for dilution of complex biological mixtures: application in 1H NMR metabonomics, Anal Chem 78(13):4281-90.
Freund, 1997, A decision-theorectic generalization of on-line learning and an application to boosting, J Comp Sys Sci, 55:119, 35 pages.
International Search Report and Written Opinion issued in International Application No. PCT/US2020/026386, date of mailing: Sep. 24, 2020, 8 pages.
Krizhevsky, 2012, Imagenet classification with deep convolutional neural networks, in Pereira, Advances in Neural Information Processing Systems, 1097-3105.
Rowjewski et al., GMP-Compliant Isolation and Expansion of Bone Marrow-Derived MSCs in the Closed, Automated Device Quantum Cell Expansion System, Cell Transplantation, Nov. 1, 2013, vol. 22, Iss. 11, pp. 1981-2000.
Simonyan, 2014, Very deep convolutional networks for large-scale image recognition, CoRR, arXiv:1409.1556v6, 14 pages.
Szegedy, 2015, Going deeper with cnvolutions, in CVPR2015, 9 pages.
Wang, 2015, Face Search at Scale: 80 Million Gallery, arXiv:1507.07242v2, 14 pages.
Search Report issued by the United Arab Emirates Ministry of Economy in Application No. P6001808/2021, date of mailing: Feb. 15, 2024, 2 pages.
Exam Report issued in New Zealand Application No. 781983, date of mailing: Jan. 24, 2025, 10 pages.

* cited by examiner

CELL CULTURE SYSTEMS AND USES THEREOF

CROSS-REFERENCE TO RELATED APPLICATIONS

This application is a national stage entry of PCT/US2020/026386 with an International Filing Date of Apr. 2, 2020, which claims the benefit of, and priority to, U.S. Provisional Patent Application No. 62/828,696, filed Apr. 3, 2019, the contents of each of which are incorporated by reference herein in their entireties.

FIELD OF THE INVENTION

The invention generally relates to cell culture methods and systems.

BACKGROUND

Cell culture is a vital tool in biological research and is used in research related to cancer, vaccines, and protein therapeutics. The process of cell culture involves maintaining cells outside of their original body under precise conditions.

Typically, lab technicians follow an already-existing protocol for a particular cell type when conducting a cell culture procedure. However, existing cell culture procedures involve many physical steps conducted by the lab technicians, extensive monitoring, and are tedious and time-consuming. The lack of automation and imputed bias from lab technicians, namely the use of already-in-place cell culture protocols without any added input, deters development and optimization of cell culture procedures.

SUMMARY

The invention provides methods and systems of determining cell culture protocols to provide a tailored cell culture procedure. Devices according to the invention are outfitted with sensors and controllers to allow for monitoring and control of precise cell culture conditions. Moreover, systems of the invention are configured to communicate with databases containing data related to cell culture procedures. Systems and methods of the invention use the data obtained from the databases, real-time feedback from the sensors, or a combination thereof, to determine, and optionally optimize, the cell culture procedure at hand and provide a tailored cell culture procedure. Moreover, data from the tailored cell culture procedure may, in turn, be stored in a database and used for future cell culture procedures.

By communicating with one or more databases, cell culture procedure data from the databases can be reviewed, analyzed, and considered for use of the data as input for tailoring of the cell culture procedure at hand. For example, the database may be a publicly available database that has an infinite number of cell culture protocol data available or the database may instead be an internal database, such as a database containing information on cell culture procedures already conducted for that cell type. In some instances, a combination of public and internal databases is accessed and information is pulled from both databases to create a tailored cell culture protocol. Systems and methods of the invention then use that input, optionally along with real-time feedback data from sensors, to create, carry-out, and optionally optimize the cell culture procedure, thereby carrying out a tailored, or personalized, cell culture procedure. Notably, the invention considers data from databases and provides a customized cell culture procedure in a timely manner. If a lab technician considered even a fraction of data from the infinite number of cell culture protocol data available from a public database, the duration of determining the cell culture procedure at hand would increase exponentially.

In certain embodiments, the process in entirely automated, without any interference or input from a lab technician. In other embodiments, input from a lab technician may be helpful or required. In such embodiments, systems of the invention may be designed to have alerting capabilities, monitoring capabilities, and/or decision-making capabilities. By providing such capabilities to systems of the invention, user (e.g., lab technician) input is kept to a minimum, saving countless hours and any bias the user may have, such as from past cell culture experiments, in determining the cell culture procedure.

In some embodiments of the invention, the cell culture systems, devices, and methods have alerting capabilities. For example, if levels of pH, dissolved oxygen, total biomass, cell diameter, or temperature fall outside user-specified or system-learned ranges, the system sends an alert to the user. In some cases, the alert may have a terminal form of an email alert, voice alert, text alert, or combination thereof.

In some embodiments of the invention, the systems, devices, and methods have monitoring capabilities. For example, profiles of pH, dissolved oxygen, total biomass, cell diameter, and temperature are read off the system. The profiles may be transmitted to a network, such as the cloud, where the profiles may be retrieved by any compatible device (e.g. smartphone) in a continuous readout format.

In certain embodiments of the invention, the systems, devices, and methods have decision-making capabilities. For example, if levels of pH, dissolved oxygen, total biomass, cell diameter, or temperature fall outside user-specified or system-learned thresholds, the system makes a decision. Examples of the decision include deciding to terminate the culture process, to stop using further reagents, to alert the user, and to shut the system down.

Certain aspects of the invention are directed to systems for monitoring and controlling cell culture. The systems comprise a cell culture apparatus operably associated with a controller. The controller comprises a hardware processor coupled to memory containing instructions executable by the processor to cause the controller to receive data associated with cells to be cultured; connect to one or more databases to receive cell culture protocol data; and determine a cell culture protocol for the cells to be cultured.

The controller may be any suitable controller. In an embodiment of the invention, the controller is integrated. In other embodiments, the controller is distributed.

Some embodiments of the invention are directed to single-use components. In some examples, the cell culture apparatus is a single-use cell culture apparatus. In certain examples, the cell culture apparatus comprises one or more sensors communicatively coupled to the controller to provide data on the cells. In some examples of the invention, the one or more sensors are single-use sensors.

In an embodiment of the invention, the controller is further configured to update the cell culture protocol based on feedback from the one or more sensors during cell culture. Feedback may be any suitable feedback from the sensors. In an embodiment, the feedback is associated with at least one of pH, glucose concentration, lactate concentration, dissolved oxygen, total biomass, cell diameter, temperature, cell type, media type, and fluid flow rate.

Any suitable database may be used in systems of the invention connected to in order to receive cell culture protocol data. In an embodiment, the one or more databases is a database comprising one or more cell culture protocols previously developed by the system. In an embodiment, the one or more databases is a publicly available database comprising one or more cell culture protocols. A person skilled in the art would recognize which database is suitable for use with the invention. For example, a skilled person may use the cell culture database described in Cell-culture Database: Literature-based reference tool for human and mammalian experimentally based cell culture applications; Amirkia and Qiubao, Bioinformation, 2012, 8(5): 237-238, incorporated herein in its entirety by reference.

Certain aspects of the invention are directed to methods of determining a cell culture protocol. The methods comprise receiving data associated with cells to be cultured; connecting to one or more databases to receive data about cell culture protocols; and determining a cell culture protocol for the cells to be cultured.

In some embodiments of the invention, methods further comprise updating the cell culture protocol based on feedback during cell culture. The feedback is from one or more sensors disposed on a cell culture apparatus and communicatively coupled with a controller. In some embodiments, the feedback is associated with at least one of pH, glucose concentration, lactate concentration, dissolved oxygen, total biomass, cell diameter, temperature, cell type, media type, and fluid flow rate.

Any suitable database may be used in methods of the invention. In some embodiments, the one or more databases is a database comprising one or more cell culture protocols previously developed by a system for monitoring and controlling cell culture. In some embodiments, the one or more databases is a publicly available database comprising one or more cell culture protocols.

In some embodiments of the invention, the determined cell culture protocol is personalized based on the received data associated with cells to be cultured. In some embodiments of the invention, the determined personalized cell culture protocol is personalized based on the received data associated with cells to be cultured for the human subject.

Certain aspects of the invention are directed to methods of determining a personalized cell culture protocol. The methods comprise receiving data associated with cells to be cultured for a human subject; connecting to one or more databases to receive data about cell culture protocols; and determining a personalized cell culture protocol for cells to be cultured for the human subject. In some embodiments, methods of the invention further comprise updating the personalized cell culture protocol based on feedback during cell culture. The feedback is from one or more sensors disposed on a cell culture apparatus and communicatively coupled with a controller. In some embodiments, the feedback is associated with at least one of pH, glucose concentration, lactate concentration, dissolved oxygen, total biomass, cell diameter, temperature, cell type, media type, and fluid flow rate.

Methods of the invention further comprise reporting the determined cell culture protocol. Reports include information about the steps conducted in the tailored cell culture procedure, including the non-limiting examples of temperature, pH, media type, fluid flow rate, and duration of time for each step of the procedure. In some examples, the report is a printed report or is shown on a user display screen of the system, such as a cell phone, tablet, or laptop.

In some embodiments, systems and methods of the invention use data from a public database for use in determining the cell culture protocol. Suitable public databases comprise data for one or more cell culture protocols. In certain embodiments, systems and methods of the invention use data from an internal database for use in determining the cell culture protocol. An internal database may include information on cell protocols previously used in the lab setting. For instance, the database may include information obtained from cell apparatus settings and information from lab notebooks. Information in the internal database may include any relevant information on cell culture protocols, such as cell type, media type, pH, temperature, duration of culture steps, and fluid flow rate use during culture. In other embodiments, systems and methods of the invention use data from a combination of databases for use in determining the cell culture protocol. The databases may be publicly available databases, internal databases, or a combination thereof. In certain embodiments, systems and methods of the invention use data from one or more databases and also include feedback data from sensors for use in determining the cell culture protocol. Feedback data includes data from a plurality of sensors monitoring conditions of the cell culture procedure.

In certain embodiments, a controller operably associated with a cell culture apparatus receives data associated with cells to be cultured, such as the cell type. The controller then connects to a database, which may be any suitable public or internal database comprising one or more cell culture protocols. The controller receives cell culture protocol data from the database and uses the data to determine the cell culture protocol at hand. In some cases, the determined cell culture protocol comprises a protocol pulled directly from a public database or internal database. In some cases, the determined cell culture protocol may be instantly used for cell culture. The determined cell culture protocol may also be stored for future use, such as being stored in an internal database.

In some cases, the controller may also receive data from the plurality of sensors on the cell culture apparatus, such as temperature, pressure, pH, temperature, and fluid flow rate. The data obtained from the sensors is used to modify the cell culture protocol obtained from the database, thereby determining a cell culture protocol based on the data obtained from the database and feedback data. Such determined cell culture protocol may be instantly used for cell culture. The determined cell culture protocol may also be stored for future use, such as in an internal database

DETAILED DESCRIPTION

The invention provides methods and systems for cell culture that can provide a tailored, or personalized, cell culture procedure. Methods of the invention include determining a cell culture protocol. In methods of the invention, data associated with cells to be cultured is received. Systems of the invention then connect to one or more databases to receive data about cell culture protocols. Additionally, devices used for the cell culture procedure may be optionally outfitted with a plurality of sensors. The sensors are communicatively coupled to a controller. The sensors provide real-time data related to the cell culture conditions. The data obtained from the one or more databases, is used to determine a cell culture protocol for the cells to be cultured, and optionally, the data obtained from the real-time feedback from the sensors, may be used to optimize or adjust the cell culture protocol that is being carried-out. That protocol, adjusted by the sensor feedback, may then be stored as a new cell culture protocol for future cell culture.

By providing such devices, systems and methods, the present invention allows for a culture procedure that is tailored, customized, and optionally optimized. Such an approach avoids extensive interaction and input from laboratory technicians in determining the cell culture protocol. In turn, the data related to such a tailored cell culture procedure may be stored in a database, such as an internal database, for use in carrying-out, developing, and determining future cell culture procedures.

Figure 1:
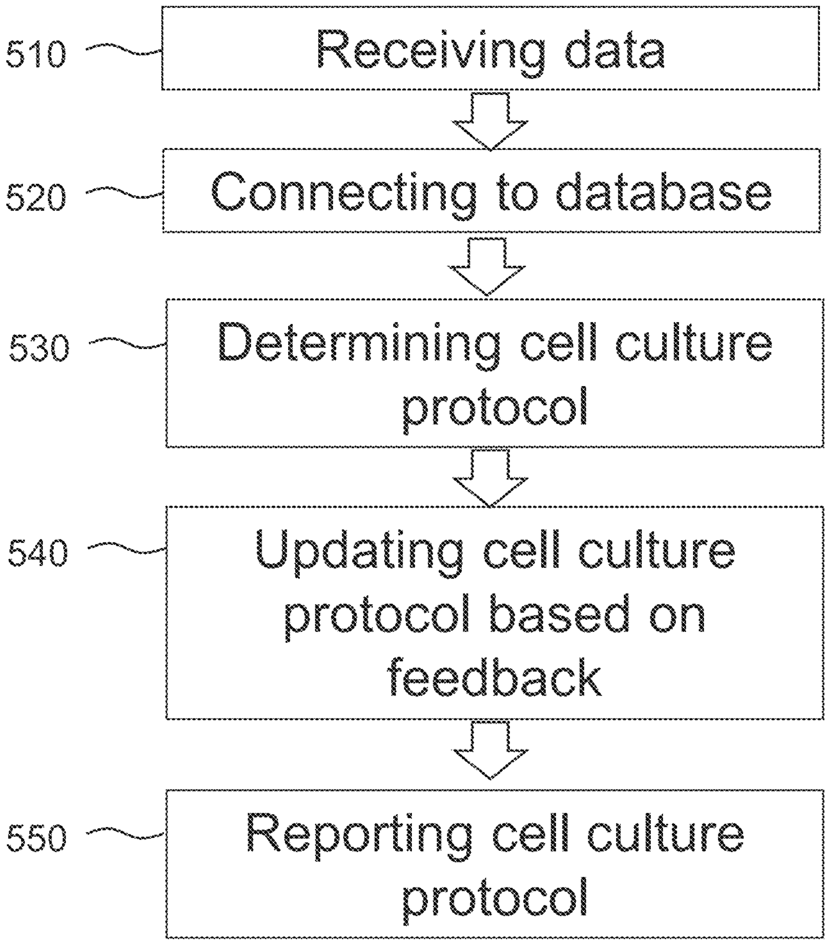
FIG. 1 diagrams a method for cell culture according to an embodiment of the invention.

FIG. 1 diagrams a method of determining a cell culture protocol. Methods according to the invention comprise 510 receiving data associated with cells to be cultured. Data may include any suitable data, such as the non-limiting examples of type of cells, number of cells, pH, temperature, and type of media.

Methods further comprise 520 connecting to one or more databases to receive data about cell culture protocols. Any suitable database may be used in methods of the invention. In some embodiments, the one or more databases is a database comprising one or more cell culture protocols previously developed by a system for monitoring and controlling cell culture. In some embodiments, the one or more databases is a publicly available database comprising one or more cell culture protocols.

Methods further comprise 530 determining a cell culture protocol for the cells to be cultured. In embodiments of the invention, machine learning is used to determine the cell culture protocol. The initial data about the cells is provided, and machine learning is used to analyze the data from one or more databases and correlate that data from the database to the initial data to determine, tailor, and optionally optimize, the cell culture protocol.

In some embodiments of the invention, methods further comprise 540 updating the cell culture protocol based on feedback during cell culture. The feedback is from one or more sensors disposed on a cell culture apparatus and communicatively coupled with a controller. In some embodiments, the feedback is associated with at least one of pH, glucose concentration, lactate concentration, dissolved oxygen, total biomass, cell diameter, temperature, cell type, media type, and fluid flow rate. In some embodiments of the invention, the determined cell culture protocol is personalized based on the received data associated with cells to be cultured.

Methods of the invention further comprise 550 reporting the determined cell culture protocol. Any suitable reporting method may be used. In some embodiments, the cell culture systems have alerting capabilities. For example, if levels of pH, dissolved oxygen, total biomass, cell diameter, or temperature fall outside user-specified or system-learned ranges, the system sends an alert to the user. In some cases, the alert may have a terminal form of an email alert, voice alert, text alert, or combination thereof. In some embodiments of the invention, the systems and methods have monitoring capabilities. For example, profiles of pH, dissolved oxygen, total biomass, cell diameter, and temperature are read off the system. The profiles may be transmitted to a network, such as the cloud, where the profiles may be retrieved by any compatible device (e.g. smartphone) in a continuous readout format. In certain embodiments of the invention, the systems and methods have decision-making capabilities. For example, if levels of pH, dissolved oxygen, total biomass, cell diameter, or temperature fall outside user-specified or system-learned thresholds, the system makes a decision. Examples of the decision include deciding to terminate the culture process, to stop using further reagents, to alert the user, and to shut the system down.

Certain aspects of the invention are directed to methods of determining a personalized cell culture protocol. The methods comprise receiving data associated with cells to be cultured for a human subject; connecting to one or more databases to receive data about cell culture protocols; and determining a personalized cell culture protocol for cells to be cultured for the human subject. In some embodiments, methods of the invention further comprise updating the personalized cell culture protocol based on feedback during cell culture. The feedback is from one or more sensors disposed on a cell culture apparatus and communicatively coupled with a controller. In some embodiments, the feedback is associated with at least one of pH, glucose concentration, lactate concentration, dissolved oxygen, total biomass, cell diameter, temperature, cell type, media type, and fluid flow rate. In some embodiments of the invention, the determined personalized cell culture protocol is personalized based on the received data associated with cells to be cultured for the human subject. Methods of the invention further comprise reporting the determined personalized cell culture protocol.

For example, systems and methods of the invention may be used for generation of cell-based immunotherapeutic products. The steps in generating cellular therapeutic product include the co-culture of stimulated antigen-presenting cells with T-cell containing cells in a biological reactor containing a cell culture chamber. A supernatant containing expanded therapeutic T-cell products is generated during culture. In certain aspects, in order to produce a quantity of antigen-specific T-cells sufficient to elicit a therapeutic response in a patient, the T-cells must undergo additional culture in one or more additional cell culture chambers. In order to effectuate this additional culture, the transfer of supernatant from the culture chamber in which the supernatant was generated to a subsequent cell culture chamber containing a fresh supply of antigen-presenting cells must occur. The transfer of supernatant between cell culture chambers may involve the introduction of a gas flow into the first cell culture chamber that transfers the supernatant comprising the first cell product through a fluidic connector and into the new cell culture chamber. Furthermore, during each of the culture steps, perfusion fluid containing, for example, medium and cytokines, can be perfused to the chambers. In certain aspects, the perfusion fluid flows through the chambers along a vertical flow path so as to ensure that the cells remain within the chamber during culture. In certain embodiments of the invention, the cells are harvested. Cell harvest is typically accomplished by injecting cold buffer into the cartridge. In some embodiments of the invention, a Peltier device may be integrated under the cartridge to cool the cartridge down to somewhere between about 20° C. to about 30° C., which allows for release without the need to dilute the cells down in a greater fluid volume.

Figure 2:
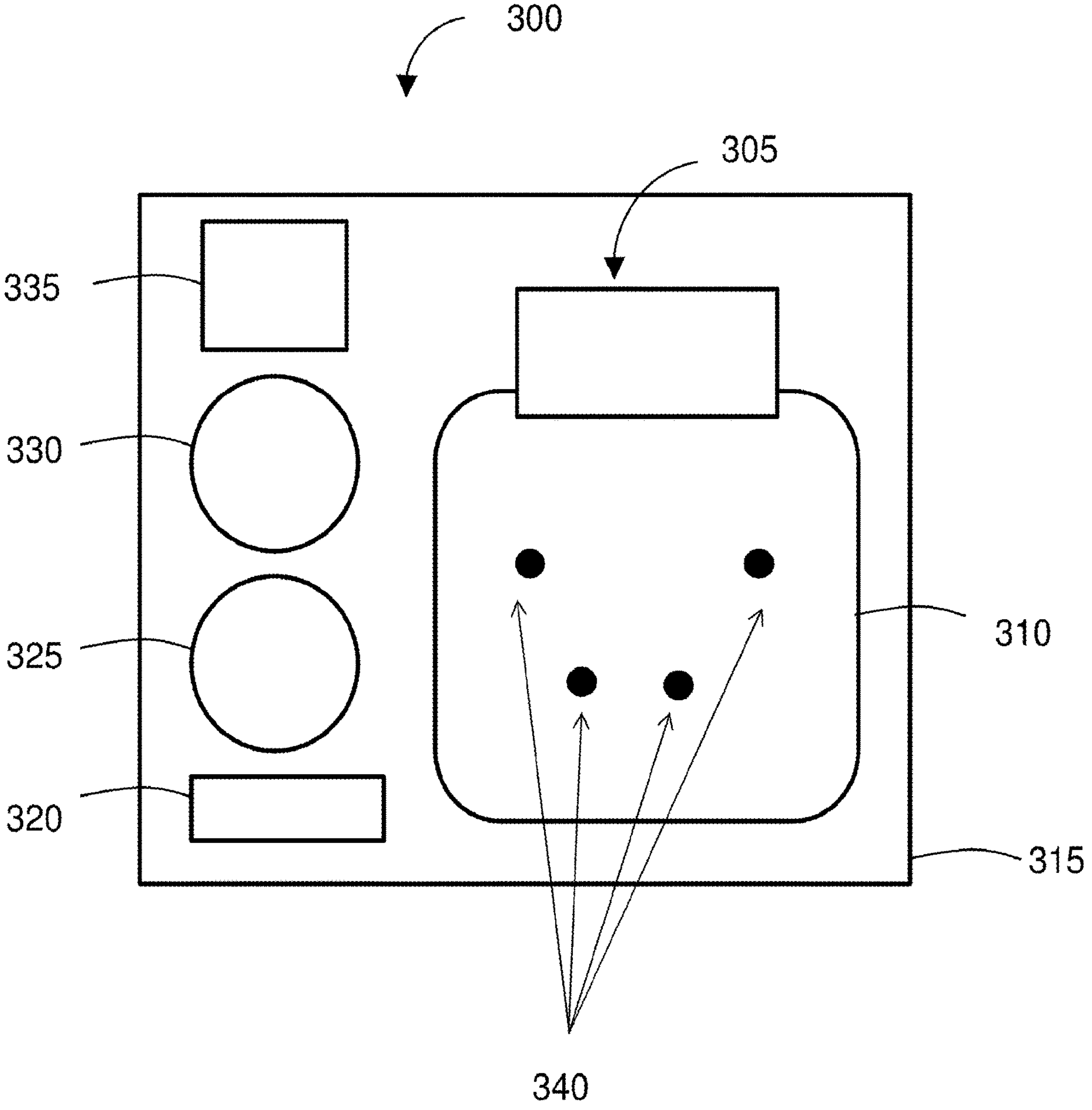
FIG. 2 shows an embodiment of a system of the invention with an integrated controller.
Figure 3:
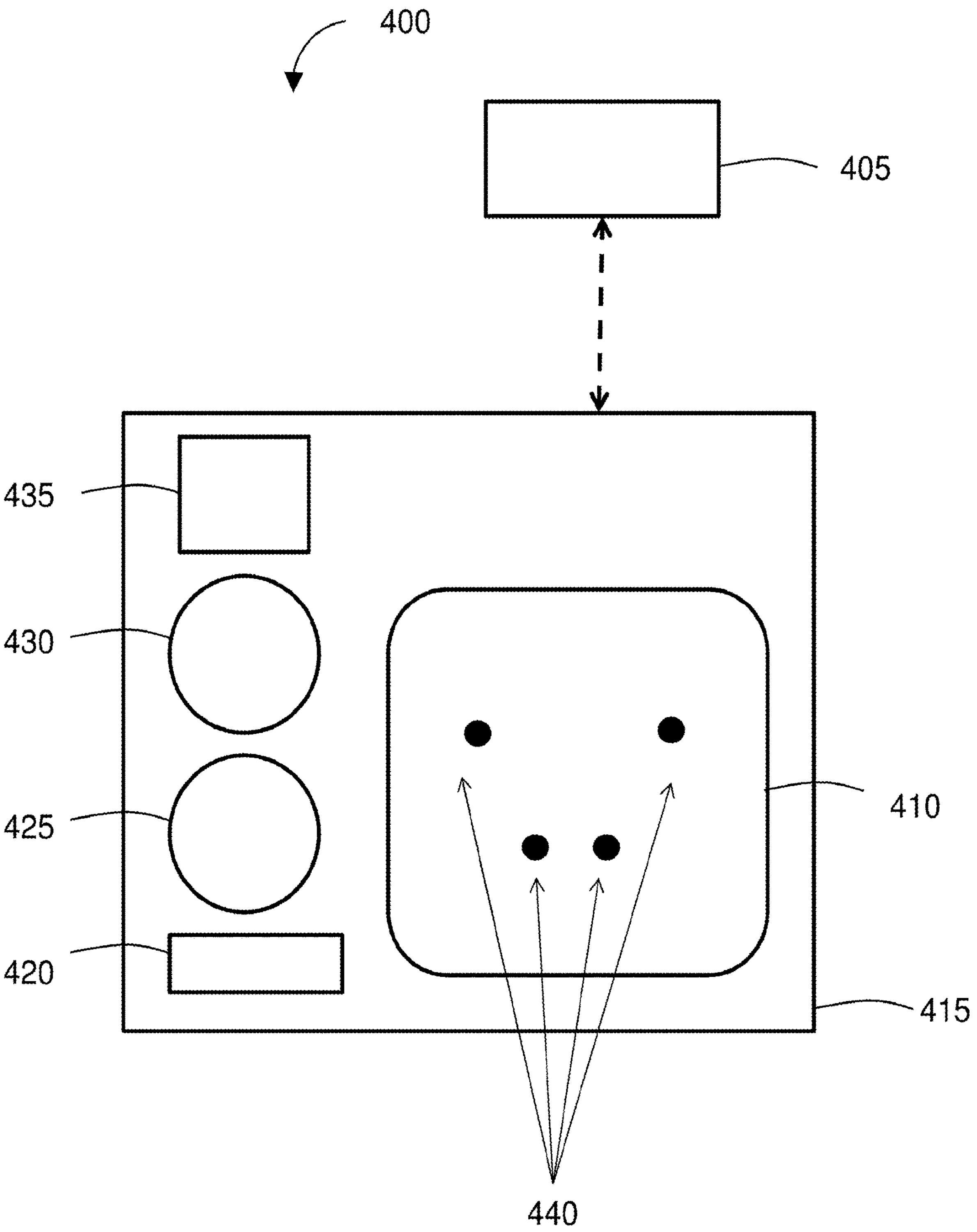
FIG. 3 shows an embodiment of a system of the invention with a distributed controller.

Certain aspects of the invention are directed to systems for monitoring and controlling cell culture, such as the non-limiting embodiments shown in FIG. 2 and FIG. 3. The systems comprise a cell culture apparatus operably associated with a controller. The controller comprises a hardware processor coupled to memory containing instructions executable by the processor to cause the controller to receive data associated with cells to be cultured; connect to one or more databases to receive cell culture protocol data; and determine a cell culture protocol for the cells to be cultured. The controller may be any suitable controller. In an embodiment of the invention, the controller is integrated. In other embodiments, the controller is distributed.

Some embodiments of the invention are directed to single-use components. By providing single-use components, sterility of the system may be maintained and the system may be customized to the cell culture procedure desired for the specified cells. In some examples, the cell culture apparatus is a single-use cell culture apparatus, or cell culture cartridge. In certain examples, the cell culture apparatus comprises one or more sensors communicatively coupled to the controller to provide data on the cells. In some examples, the one or more sensors are single-use sensors.

In an embodiment of the invention, the controller is further configured to update the cell culture protocol based on feedback from the one or more sensors during cell culture. Feedback may be any suitable feedback from the sensors. In an embodiment, the feedback is associated with at least one of pH, glucose concentration, lactate concentration, dissolved oxygen, total biomass, cell diameter, temperature, cell type, media type, and fluid flow rate. In some embodiments of the invention, the determined cell culture protocol is personalized based on the received data associated with cells to be cultured.

Any suitable database may be used in systems of the invention connected to in order to receive cell culture protocol data. Cell culture protocol data includes cell type, effective media and antibiotics, concentrations of media and antibiotics, and conditions for culture, such as temperature, pH, fluid flow rate, pressure. A person skilled in the art would recognize which database is suitable for use with the invention.

In an embodiment, the one or more databases is a database comprising one or more cell culture protocols previously developed by the system. Such a database may be described as an internal database. Information contained in the database may be obtained from lab notebooks or settings input in a cell culture apparatus. The database may contain information on cell culture protocols, such as the cell type, media type, temperature, pH, pressure, fluid flow rate, and duration of culture steps.

In an embodiment, the one or more databases is a publicly available database comprising one or more cell culture protocols. In some embodiments, a skilled person may use the cell culture database described in Amirkia and Qiubao, Cell-culture Database: Literature-based reference tool for human and mammalian experimentally based cell culture applications; Bioinformation, 2012; 8(5): 237-238, incorporated herein in its entirety by reference. The Cell-culture Database is publicly available at cell-lines.toku-e.com and is helpful for choosing the most effective media and antibiotics for cells, determining concentrations and combinations of antibiotics for selection and transfection experiments, and locating literature relevant to cell lines of interest or plasmids or vectors of interest. To use the Cell-culture Database, the name of a cell line, plasmid, or vector is entered in a search box and relevant data is browsed. The database provides information about other experiments which have used the same cell lines or plasmid, such as what other media has been used to grow the cells in question.

In some embodiments, data from a database is not available for use. For example, if an experiment is being run for the first time or if a certain type of cells are being cultured for the first time. In such an embodiment, methods and systems of the invention optimize the cell culture protocol by sensing a user-defined parameter throughout the cell culture process and implement changes to the protocol to maintain a set level of the user-defined parameter.

In an embodiment, methods of optimizing a cell culture protocol comprise receiving data associated with cells to be cultured. A user-defined parameter is set at a level to be maintained during cell culture. The user-defined parameter comprises pH, turbidity, glucose concentration, lactate concentration, other measures of cell health or identity, or a combination thereof. A cell culture protocol is implemented, and the level of the user-defined parameter is measured during cell culture. The level of the parameter may be measured periodically during the cell culture protocol. The cell culture protocol is optimized by determining whether to change cell culture conditions to maintain the level of the user-defined parameter. In some instances, methods comprise changing cell culture conditions. In an example, changing cell culture conditions comprises manipulating a flow rate of media to change glucose concentration or lactate concentration. In another example, changing cell culture conditions comprises adding supplements. Supplements comprise cytokines, growth factors, and serum. Methods further comprise storing the optimized cell protocol in a database for future use.

FIG. 2 shows an embodiment of a system 300 of the invention. A controller 305 is integrated. The controller 305 and cell culture cartridge 310 are shown arranged on a console 315. Sensors 340 are disposed on the cell culture cartridge 310 for monitoring of conditions. The controller 305 is communicatively coupled with one or more sensors 340. The controller 305 is communicatively coupled with a peristaltic pump 335 used to pump fluid into and out of the cell culture cartridge 310. The cell culture cartridge 310 has a bottom surface to which cells adhere. In other embodiments, cells do not adhere to the bottom surface. The cell culture cartridge 310 has one or more fluid inlets and one or more fluid outlets. Connective tubing (not shown) connects the fluid inlets with the differentiation medium reservoir (perfusion source) 325 containing differentiation medium. The differentiation medium reservoir 325 contains differentiation medium that will be pumped into the cell culture cartridge 310. Connective tubing also connects the fluid outlet with the waste reservoir 330. Depleted medium will be pumped out of the cell culture cartridge 310 through the outlet and into the waste reservoir 330. In some instances, lids on the differentiation medium reservoir 325 and the waste reservoir 330 are not removable, thereby maintaining a sterile system. In other embodiments, the lids are removable. Stopcocks and/or luer activated valves (LAVs) on the reservoir bottles 325 and 330 allow for sterile transfer of differentiation medium to fill the inlet bottle and remove waste from the outlet bottle. The console 315 provides designated spaces for arrangement of the previously mentioned components and also provides a display/userface 320, connection, and on/off switch.

FIG. 3 shows an embodiment of a system 400 of the invention. A controller 405 is distributed. The controller 405 and cell culture cartridge 410 are shown arranged on a console 415. Sensors 440 are disposed on the cell culture cartridge 410 for monitoring of conditions. The controller 405 is communicatively coupled with one or more sensors 440. The controller 405 is communicatively coupled with a peristaltic pump 435 used to pump fluid into and out of the cell culture cartridge 410. The cell culture cartridge 410 has a bottom surface to which cells adhere. In other embodiments, cells do not adhere to the bottom surface. The cell culture cartridge 410 has one or more fluid inlets and one or more fluid outlets. Connective tubing (not shown) connects the fluid inlets with the differentiation medium reservoir (perfusion source) 425 containing differentiation medium. The differentiation medium reservoir 425 contains differentiation medium that will be pumped into the cell culture cartridge 410. Connective tubing also connects the fluid outlet with the waste reservoir 430. Depleted medium will be pumped out of the cell culture cartridge 410 through the outlet and into the waste reservoir 430. In some instances, lids on the differentiation medium reservoir 425 and the waste reservoir 430 are not removable, thereby maintaining a sterile system. In other embodiments, the lids are removable. Stopcocks and/or luer activated valves (LAVs) on the reservoir bottles 425 and 430 allow for sterile transfer of differentiation medium to fill the inlet bottle and remove waste from the outlet bottle. The console 415 provides designated spaces for arrangement of the previously mentioned components and also provides a display/userface 420, connection, and on/off switch.

The cartridge may be constructed out of any suitable material. In some instances, the cartridge is constructed from polystyrene, acrylate, or a combination thereof. As an example, the base or bottom surface comprises polystyrene and the top surface and side surfaces are acrylate. As another example, for high volume manufacturing, the cartridge may be made entirely of polystyrene.

In one example embodiment, the bottom surface comprises polystyrene and/or acrylate. The use of the same polystyrene surface for dendritic cell (DC) production all the way through one cycle of T-cell stimulation is tremendously valuable from a bioprocess standpoint, as it eliminates a large number of transfer steps that would otherwise be necessary, thereby allowing for a closed system for DC-stimulated therapeutic T-cell manufacturing.

Furthermore, any suitable material treatment may be performed on the cartridge. In some embodiments, the bottom polystyrene surface may be modified to facilitate cell adhesion. For example, the bottom polystyrene surface may undergo treatment with an air or oxygen plasma, also known as glow discharge or corona discharge. For example, the bottom polystyrene surface may undergo modification with proteins or poly-amino acids that are known to facilitate cell adhesion, including but not limited to fibronectin, laminin, and collagen.

The bottom surface can have a surface area comparable to conventional well plates, such as 6- and 24-well plates (9.5 $cm^2$ and 1.9 $cm^2$, respectively) or T flasks (25 $cm^2$ to 225 $cm^2$). It is also to be understood that the surface area can be smaller or even much larger than conventional well plates (e.g., having surface areas comparable to standard cell culture dishes and flasks), such as having a surface area between about 2.0 $cm^2$ and about 500 $cm^2$, for example, about 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 25.0, 30.0, 35.0, 40.0, 45.0, 50.0, 55.0, 60.0, 65.0, 70.0, 75.0, 100.0, 125.0, 150.0, 175.0, 200.0, 400.0, 500.0 $cm^2$, and any surface area in between, where the surfaces can be rigid (flask) or flexible (bag).

The surfaces of the cell culture cartridge can be joined together using any methods known in the art, such as mechanical fastening, adhesive and solvent bonding, and welding. However, given that the cellular immunotherapeutic product produced using systems and methods of embodiments of the invention will be administered to a human patient, regulatory issues may prevent the use of certain, or all, adhesives in assembling the cell culture chambers. Accordingly, in certain embodiments, the surfaces are joined without using adhesive. In one embodiment, all surfaces of the cell culture chamber, such as the bottom, side, and top walls, comprise the first material (e.g., polystyrene) and are joined together using ultrasonic welding. It is to be understood that the aforementioned configurations are only examples and that other configurations for joining the surfaces are also contemplated embodiments of the present invention.

The height of the one or more cell culture chambers can vary. For example, and not limitation, an example range of cell culture chamber heights includes heights of anywhere from 0.5 mm to 100 mm, such as 0.5, 1.0, 2.0, 3.0, 4.0, 5.0, 6.0, 7.0, 8.0, 9.0, 10.0, 15.0, 20.0, 25.0, 30.0, 35.0, 40.0, 45.0, 50.0, 55.0, 60.0, 65.0, 70.0, 75.0, 80.0, 85.0, 90.0, 95.0, 100.0 mm, or more, or any height therebetween. In certain embodiments, the heights of the chamber can be comparable to liquid heights in cultures that are typically performed in 6- and 24-well plates, such as between 2 and 6 mm, with a volume capacity of about 0.8 mL to 6 mL. In other embodiments, the cell culture chambers will be of large size, such as between 10 mm and 50 mm, with a culture surface of about 50 $cm^2$.

In some embodiments of the invention, the cartridges are optically clear or transparent. Such optical clarity, in combination with the fluidic ports being segregated appropriately, allows a user to view cells at any vertical plane within the cartridge. Further, stopcocks may be placed on the cartridge or on the reservoir bottles. In particular, stopcocks may be placed at specific ports on the cartridge and each serves a specific function. Placement is specific to each function, and work was performed to determine the optimal locations to ensure that the process is successful and workflow is easy. For example, stopcocks may be used for seeding and harvesting, and a luer activated valve (LAV) on top of stopcock allows for syringe to be sterilely connected. Stopcocks may be used for seeding and harvesting (adding cold buffer for washes), and air inside the cartridge will flow out through the filter at this stopcock as cell solution is seeded into the cartridge. As another example, stopcocks may be used for harvest, and air inside the cartridge will flow into the cartridge as cell solution is removed. The filters attached to the stopcocks avoid pressure or vacuum buildup within cartridge as liquid is being added or removed from cartridge. In the invention, LAVs may be used on the bottles to add and/or remove medium. Traditionally, LAVs are sold and marketed to be used for anesthesia and IV lines. Therefore, using the LAVs for addition or removal of medium departs from traditional use.

Aspects of the present disclosure described herein, such as control of the movement of fluid through the system, as described above, and the monitoring and controlling of various parameters, can be performed using any type of computing device, such as a computer or programmable logic controller (PLC), that includes a processor, e.g., a central processing unit, or any combination of computing devices where each device performs at least part of the process or method. In some embodiments, systems and methods described herein may be performed with a handheld device, e.g., a smart tablet, a smart phone, or a specialty device produced for the system.

Methods of the present disclosure can be performed using software, hardware, firmware, hardwiring, or combinations of any of these. Features implementing functions can also be physically located at various positions, including being distributed such that portions of functions are implemented at different physical locations (e.g., imaging apparatus in one room and host workstation in another, or in separate buildings, for example, with wireless or wired connections).

Processors suitable for the execution of computer program include, by way of example, both general and special purpose microprocessors, and any one or more processor of any kind of digital computer. Generally, a processor will receive instructions and data from a read-only memory or a random access memory or both. Elements of computer are a processor for executing instructions and one or more memory devices for storing instructions and data. Generally, a computer will also include, or be operatively coupled to receive data from or transfer data to, or both, one or more non-transitory mass storage devices for storing data, e.g., magnetic, magneto-optical disks, or optical disks. In some embodiments, sensors on the system send process data via Bluetooth to a central data collection unit located outside of an incubator. In some embodiments, data is sent directly to the cloud rather than to physical storage devices. Information carriers suitable for embodying computer program instructions and data include all forms of non-volatile memory, including by way of example semiconductor memory devices, (e.g., EPROM, EEPROM, solid state drive (SSD), and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having an I/O device, e.g., a CRT, LCD, LED, or projection device for displaying information to the user and an input or output device such as a keyboard and a pointing device, (e.g., a mouse or a trackball), by which the user can provide input to the computer. Other kinds of devices can be used to provide for interaction with a user as well. For example, feedback provided to the user can be any form of sensory feedback (e.g., visual feedback, auditory feedback, or tactile feedback), and input from the user can be received in any form, including acoustic, speech, or tactile input.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and front-end components. The components of the system can be interconnected through network by any form or medium of digital data communication, e.g., a communication network. Examples of communication networks include cell network (e.g., 3G, 4G, or 5G), a local area network (LAN), and a wide area network (WAN), e.g., the Internet.

The subject matter described herein can be implemented as one or more computer program products, such as one or more computer programs tangibly embodied in an information carrier (e.g., in a non-transitory computer-readable medium) for execution by, or to control the operation of, data processing apparatus (e.g., a programmable processor, a computer, or multiple computers). A computer program (also known as a program, software, software application, app, macro, or code) can be written in any form of programming language, including compiled or interpreted languages (e.g., C, C++, Perl), and it can be deployed in any form, including as a stand-alone program or as a module, component, subroutine, or other unit suitable for use in a computing environment. Systems and methods of the invention can include instructions written in any suitable programming language known in the art, including, without limitation, C, C++, Perl, Java, ActiveX, HTML5, Visual Basic, or JavaScript.

A computer program does not necessarily correspond to a file. A program can be stored in a file or a portion of file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

A file can be a digital file, for example, stored on a hard drive, SSD, CD, or other tangible, non-transitory medium. A file can be sent from one device to another over a network (e.g., as packets being sent from a server to a client, for example, through a Network Interface Card, modem, wireless card, or similar).

Writing a file according to embodiments of the invention involves transforming a tangible, non-transitory, computer-readable medium, for example, by adding, removing, or rearranging particles (e.g., with a net charge or dipole moment into patterns of magnetization by read/write heads), the patterns then representing new collocations of information about objective physical phenomena desired by, and useful to, the user. In some embodiments, writing involves a physical transformation of material in tangible, non-transitory computer readable media (e.g., with certain optical properties so that optical read/write devices can then read the new and useful collocation of information, e.g., burning a CD-ROM). In some embodiments, writing a file includes transforming a physical flash memory apparatus such as NAND flash memory device and storing information by transforming physical elements in an array of memory cells made from floating-gate transistors. Methods of writing a file are well-known in the art and, for example, can be invoked manually or automatically by a program or by a save command from software or a write command from a programming language.

Suitable computing devices typically include mass memory, at least one graphical user interface, at least one display device, and typically include communication between devices. The mass memory illustrates a type of computer-readable media, namely computer storage media. Computer storage media may include volatile, nonvolatile, removable, and non-removable media implemented in any method or technology for storage of information, such as computer readable instructions, data structures, program modules, or other data. Examples of computer storage media include RAM, ROM, EEPROM, flash memory, or other memory technology, CD-ROM, digital versatile disks (DVD) or other optical storage, magnetic cassettes, magnetic tape, magnetic disk storage or other magnetic storage devices, Radiofrequency Identification (RFID) tags or chips, or any other medium which can be used to store the desired information and which can be accessed by a computing device.

As one skilled in the art would recognize as necessary or best-suited for performance of the methods of the invention, a computer system or machines employed in embodiments of the invention may include one or more processors (e.g., a central processing unit (CPU) a graphics processing unit (GPU) or both), a main memory and a static memory, which communicate with each other via a bus.

Figure 4:
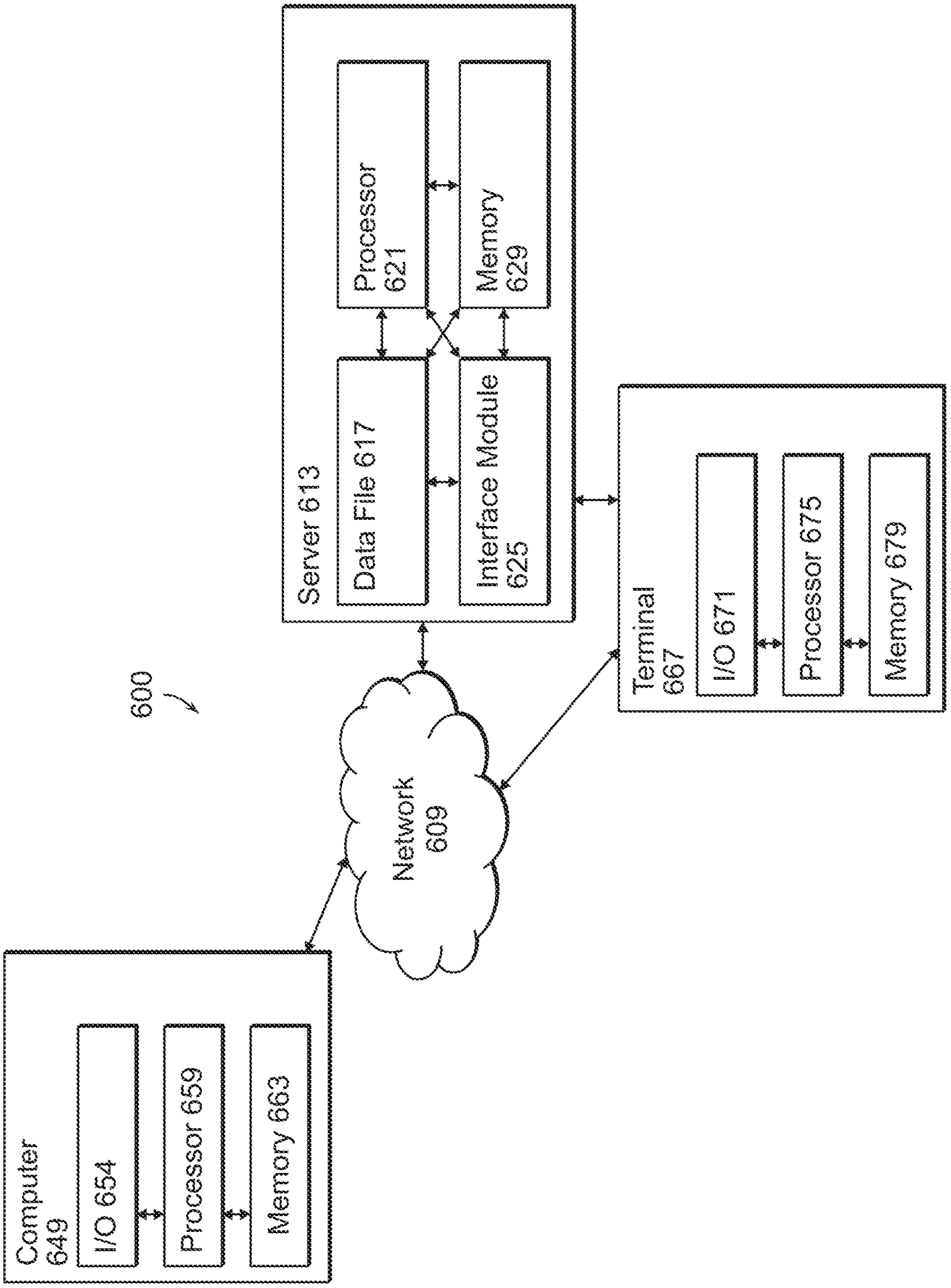
FIG. 4 shows a block diagram of a system for cell culture according to methods of the invention.

In an example embodiment shown in FIG. 4, system 600 can include a computer 649 (e.g., laptop, desktop, or tablet). The computer 649 may be configured to communicate across a network 609. Computer 649 includes one or more processor 659 and memory 663 as well as an input/output mechanism 654. Where methods of the invention employ a client/server architecture, operations of methods of the invention may be performed using server 613, which includes one or more of processor 621 and memory 629, capable of obtaining data, instructions, etc., or providing results via interface module 625 or providing results as a file 617. Server 613 may be engaged over network 609 through computer 649 or terminal 667, or server 613 may be directly connected to terminal 667, including one or more processor 675 and memory 679, as well as input/output mechanism 671.

System 600 or machines according to example embodiments of the invention may further include, for any of I/O 654 or 671 a video display unit (e.g., a liquid crystal display (LCD) or a cathode ray tube (CRT)). Computer systems or machines according to some embodiments can also include an alphanumeric input device (e.g., a keyboard), a cursor control device (e.g., a mouse), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

Memory 663, 679, or 629 according to example embodiments of the invention can include a machine-readable medium on which is stored one or more sets of instructions (e.g., software) embodying any one or more of the methodologies or functions described herein. The software may also reside, completely or at least partially, within the main memory and/or within the processor during execution thereof by the computer system, the main memory and the processor also constituting machine-readable media. The software may further be transmitted or received over a network via the network interface device.

Figure 5:
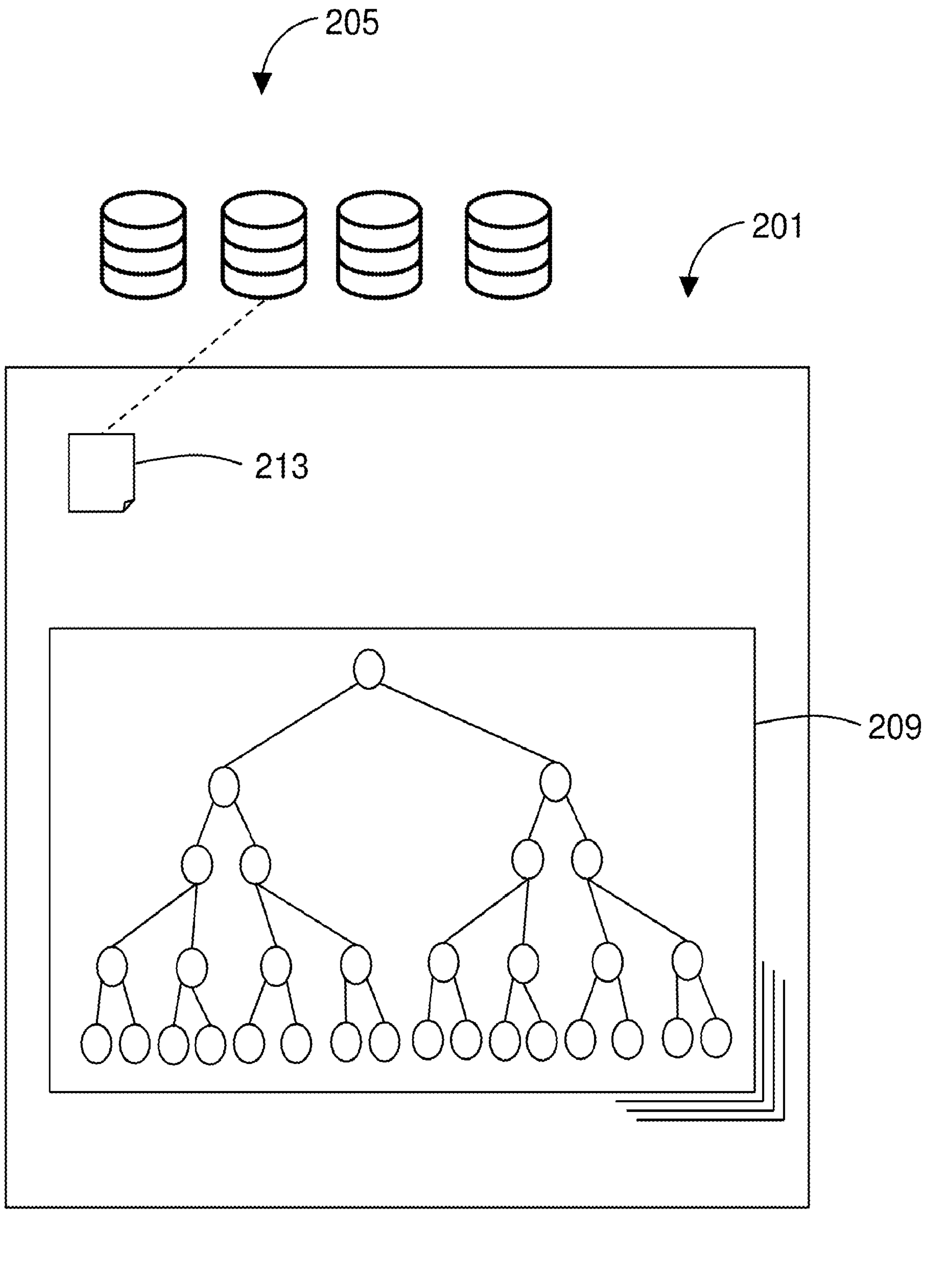
FIG. 5 shows an embodiment of a machine learning system of the invention.

FIG. 5 shows a machine learning system 201 according to certain embodiments. The machine learning system 201 accesses data from a plurality of sources 205. Any suitable source of data 205 may be provided to the machine learning system 201.

In preferred embodiments, the plurality of data sources 205 feed into the machine learning system 201. Any suitable machine learning system 201 may be used. For example, the machine learning system 201 may include one or more of a random forest, a support vector machine, a Bayesian classifier, and a neural network. In the depicted embodiment, the machine learning system 201 includes a random forest 209. In some embodiments, the computing system comprises an autonomous machine learning system that associates the functional biomarker measurements with the known cancer statuses in an unsupervised manner. The autonomous machine learning system may include a deep learning neural network that includes an input layer, a plurality of hidden layers, and an output layer. The autonomous machine learning system may represent the training data set using a plurality of features, wherein each feature comprises a feature vector.

The machine learning system 201 may access data from the plurality of sources 205 in any suitable format including, for example, as summary tables (e.g., formatted as comma separated values) or in whole (e.g., to be parsed by a script such as in Perl or SQL in the machine learning system 201). However the initial format, the data ultimately can be understood to include a plurality of entries 213. Each entry preferably includes a datum, or a value, that provides information to the system 201. The value may be a numerical value or it may be a string, such as a classification of disease code (e.g., ICD-9 code or ICD-10 code), which may be aggregated from different sources.

Most preferably, each entry 213 in the data is: specific to one data point from the protocol, and assigned to a predefined category. It will be understood that, in the case of providing a personalized cell culture protocol, the data sources 205 may provide anonymized data. In such cases, each entry 213 is preferably specific to a patient and tracked to that patient by a patient ID value, which may be a random string or code. The external data sources 205 may provide the patient ID, or the machine learning system 201 may assign a patient ID to each entry 213. Each entry 213 preferably also has a category. For example, where a data entry 213 is information or data on the initial cells, the category may be "initial" (and the value for the entry 213 is a specific data point). In another example, where a data source 205 is information or data from a publicly-available cell culture protocol database, a data entry 213 may be categorized as a database input and the value may be the specific conditions for that particular protocol, such as time, media, temperature, pH, etc. The machine learning system 201 access the plurality of data sources 205 and discovers associations therein.

Devices and methods of the disclosure may provide a user interface, e.g., in the form of a portal or dashboard. Any suitable information may be provided on the dashboard, such as running conditions of the cell culture procedure, data imported from one or more publicly-available databases, and/or data associated with feedback from the running cell culture procedure.

Discovering an association may include observing, in a plurality of cell culture procedures, co-occurrences of event categories significantly different from an expected number of co-occurrences. In certain embodiments of the invention, inputs into a machine learning algorithm are scaled or normalized to facilitate meaningful comparisons across categorically different input types. Scaling and normalization methods are included. Scaling is used to divide each individual's data by a number to achieve some goal e.g., so that the range of values for all data lies in some interval, such as [0,1].

Scaling details may include choices such as "none", "centering", "autoscaling", "rangescaling", "paretoscaling" (by default="autoscaling"). A number of different scaling methods are provided: "none": no scaling method is applied; "centering": centers the mean to zero; "autoscaling": centers the mean to zero and scales data by dividing each variable by the variance; "rangescaling": centers the mean to zero and scales data by dividing each variable by the difference between the minimum and the maximum value; "paretoscaling": centers the mean to zero and scales data by dividing each variable by the square root of the standard deviation. Unit scaling divides each variable by the standard deviation so that each variance is equal to 1.

Normalization details are included and may be used. As with scaling, normalization may be used to divide or shift the total dataset to, for example, facilitate comparison of data from unlike source or of unlike formatting. For example, one could use the z-score of the data points: $(z-\mu)/\sigma$. This normalization is determined by the mean of the data and its variance.

A number of different normalization methods are provided: "none": no normalization method is applied; "pqn": Probabilistic Quotient Normalization is computed as described in Dieterle, 2006, Probabilistic quotient normalization as robust method to account for dilution of complex biological mixtures: application in $^{1}$H NMR metabonomics, Anal Chem 78(13): 4281-90, incorporated herein by reference; "sum": samples are normalized to the sum of the absolute value of all variables for a given sample; "median": samples are normalized to the median value of all variables for a given sample; "sqrt": samples are normalized to the root of the sum of the squared value of all variables for a given sample.

Systems and methods of the disclosure include a machine learning system 201. The machine learning system 201 is preferably implemented in a tangible, computer system built for implementing methods described herein. Any machine learning algorithm may be used to analyze the data including, for example, a random forest, a support vector machine (SVM), or a boosting algorithm (e.g., adaptive boosting (AdaBoost), gradient boost method (GBM), or extreme gradient boost methods (XGBoost)), or neural networks such as H2O.

Machine learning algorithms generally are of one of the following types: (1) bagging (decrease variance), (2) boosting (decrease bias), or (3) stacking (improving predictive force). In bagging, multiple prediction models (generally of the same type) are constructed from subsets of classification data (classes and features) and then combined into a single classifier. Random Forest classifiers are of this type. In boosting, an initial prediction model is iteratively improved by examining prediction errors. AdaBoost and eXtreme Gradient Boosting are of this type. In stacking models, multiple prediction models (generally of different types) are combined to form the final classifier. These methods are called ensemble methods. The fundamental or starting methods in the ensemble methods are often decision trees. Decision trees are non-parametric supervised learning methods that use simple decision rules to infer the classification from the features in the data. They have some advantages in that they are simple to understand and can be visualized as a tree starting at the root (usually a single node) and repeatedly branch to the leaves (multiple nodes) that are associated with the classification.

In some embodiments, method and system of the invention use a machine learning system 201 that uses a random forest 209. Random forests use decision tree learning, where a model is built that predicts the value of a target variable based on several input variables. Decision trees can generally be divided into two types. In classification trees, target variables take a finite set of values, or classes, whereas in regression trees, the target variable can take continuous values, such as real numbers. Examples of decision tree learning include classification trees, regression trees, boosted trees, bootstrap aggregated trees, random forests, and rotation forests. In decision trees, decisions are made sequentially at a series of nodes, which correspond to input variables. Random forests include multiple decision trees to improve the accuracy of predictions. See Breiman, 2001, Random Forests, Machine Learning 45:5-32, incorporated herein by reference. In random forests, bootstrap aggregating or bagging is used to average predictions by multiple trees that are given different sets of training data. In addition, a random subset of features is selected at each split in the learning process, which reduces spurious correlations that can results from the presence of individual features that are strong predictors for the response variable.

SVMs can be used for classification and regression. When used for classification of new data into one of two categories, such as having a disease or not having a disease, a SVM creates a hyperplane in multidimensional space that separates data points into one category or the other. Although the original problem may be expressed in terms that require only finite dimensional space, linear separation of data between categories may not be possible in finite dimensional space. Consequently, multidimensional space is selected to allow construction of hyperplanes that afford clean separation of data points. See Press, W. H. et al., Section 16.5. Support Vector Machines. Numerical Recipes: The Art of Scientific Computing (3rd ed.). New York: Cambridge University (2007), incorporated herein by reference. SVMs can also be used in support vector clustering. See Ben-Hur, 2001, Support Vector Clustering, J Mach Learning Res 2:125-137, incorporated herein by reference.

Boosting algorithms are machine learning ensemble meta-algorithms for reducing bias and variance. Boosting is focused on turning weak learners into strong learners where a weak learner is defined to be a classifier which is only slightly correlated with the true classification while a strong learner is a classifier that is well-correlated with the true classification. Boosting algorithms consist of iteratively learning weak classifiers with respect to a distribution and adding them to a final strong classifier. The added classifiers are typically weighted in based on their accuracy. Boosting algorithms include AdaBoost, gradient boosting, and XGBoost. See Freund, 1997, A decision-theoretic generalization of on-line learning and an application to boosting, J Comp Sys Sci 55:119; and Chen, 2016, XGBoost: A Scalable Tree Boosting System, arXiv:1603.02754, both incorporated herein by reference.

Neural networks, modeled on the human brain, allow for processing of information and machine learning. Neural networks include nodes that mimic the function of individual neurons, and the nodes are organized into layers. Neural networks include an input layer, an output layer, and one or more hidden layers that define connections from the input layer to the output layer. Systems and methods of the invention may include any neural network that facilitates machine learning. The system may include a known neural network architecture, such as GoogLeNet (Szegedy, et al. Going deeper with convolutions, in CVPR 2015, 2015); AlexNet (Krizhevsky, et al. Imagenet classification with deep convolutional neural networks, in Pereira, et al. Eds., Advances in Neural Information Processing Systems 25, pages 1097-3105, Curran Associates, Inc., 2012); VGG16 (Simonyan & Zisserman, Very deep convolutional networks for large-scale image recognition, CoRR, abs/3409.1556, 2014); or FaceNet (Wang et al., Face Search at Scale: 80 Million Gallery, 2015), each of the aforementioned references are incorporated herein by reference.

Deep learning neural networks (also known as deep structured learning, hierarchical learning or deep machine learning) include a class of machine learning operations that use a cascade of many layers of nonlinear processing units for feature extraction and transformation. Each successive layer uses the output from the previous layer as input. The algorithms may be supervised or unsupervised and applications include pattern analysis (unsupervised) and classification (supervised). Certain embodiments are based on unsupervised learning of multiple levels of features or representations of the data. Higher level features are derived from lower level features to form a hierarchical representation. Those features are preferably represented within nodes as feature vectors. Deep learning by the neural network includes learning multiple levels of representations that correspond to different levels of abstraction; the levels form a hierarchy of concepts. In some embodiments, the neural network includes at least 5 and preferably more than ten hidden layers. The many layers between the input and the output allow the system to operate via multiple processing layers.

Deep learning is part of a broader family of machine learning methods based on learning representations of data. An observation can be represented in many ways such as a vector of intensity values per pixel, or in a more abstract way as a set of edges, regions of particular shape, etc. Those features are represented at nodes in the network. Preferably, each feature is structured as a feature vector, a multi-dimensional vector of numerical features that represent some object. The feature provides a numerical representation of objects, since such representations facilitate processing and statistical analysis. Feature vectors are similar to the vectors of explanatory variables used in statistical procedures such as linear regression. Feature vectors are often combined with weights using a dot product in order to construct a linear predictor function that is used to determine a score for making a prediction.

The vector space associated with those vectors may be referred to as the feature space. In order to reduce the dimensionality of the feature space, dimensionality reduction may be employed. Higher-level features can be obtained from already available features and added to the feature vector, in a process referred to as feature construction. Feature construction is the application of a set of constructive operators to a set of existing features resulting in construction of new features.

Within the network, nodes are connected in layers, and signals travel from the input layer to the output layer. In certain embodiments, each node in the input layer corresponds to a respective one of the features from the training data. The nodes of the hidden layer are calculated as a function of a bias term and a weighted sum of the nodes of the input layer, where a respective weight is assigned to each connection between a node of the input layer and a node in the hidden layer. The bias term and the weights between the input layer and the hidden layer are learned autonomously in the training of the neural network. The network may include thousands or millions of nodes and connections. Typically, the signals and state of artificial neurons are real numbers, typically between 0 and 1. Optionally, there may be a threshold function or limiting function on each connection and on the unit itself, such that the signal must surpass the limit before propagating. Back propagation is the use of forward stimulation to modify connection weights, and is sometimes done to train the network using known correct outputs. See WO 2016/182551, U.S. Pub. 2016/0174902, U.S. Pat. No. 8,639,043, and U.S. Pub. 2017/0053398, each incorporated herein by reference.

In some embodiments, datasets are used to cluster a training set. Particular exemplary clustering techniques that can be used in the present invention include, but are not limited to, hierarchical clustering (agglomerative clustering using nearest-neighbor algorithm, farthest-neighbor algorithm, the average linkage algorithm, the centroid algorithm, or the sum-of-squares algorithm), k-means clustering, fuzzy k-means clustering algorithm, and Jarvis-Patrick clustering.

Bayesian networks are probabilistic graphical models that represent a set of random variables and their conditional dependencies via directed acyclic graphs (DAGs). The DAGs have nodes that represent random variables that may be observable quantities, latent variables, unknown parameters or hypotheses. Edges represent conditional dependencies; nodes that are not connected represent variables that are conditionally independent of each other. Each node is associated with a probability function that takes, as input, a particular set of values for the node's parent variables, and gives (as output) the probability (or probability distribution, if applicable) of the variable represented by the node.

Regression analysis is a statistical process for estimating the relationships among variables such as features and outcomes. It includes techniques for modeling and analyzing relationships between a multiple variables. Specifically, regression analysis focuses on changes in a dependent variable in response to changes in single independent variables. Regression analysis can be used to estimate the conditional expectation of the dependent variable given the independent variables. The variation of the dependent variable may be characterized around a regression function and described by a probability distribution. Parameters of the regression model may be estimated using, for example, least squares methods, Bayesian methods, percentage regression, least absolute deviations, nonparametric regression, or distance metric learning.

Any suitable machine learning algorithm may be included. In some embodiments, the machine learning system 201 includes a random forest 209. The machine learning system may learn in a supervised or unsupervised fashion. A machine learning system that learns in an unsupervised fashion may be referred to as an autonomous machine learning system. While other versions are within the scope of the invention, an autonomous machine learning system can employ periods of both supervised and unsupervised learning. The random forest 209 may be operated autonomously and may include periods of both supervised and unsupervised learning. See Criminisi, 2012, Decision Forests: A unified framework for classification, regression, density estimation, manifold learning and semi-supervised learning, Foundations and Trends in Computer Graphics and Vision 7(2-3):81-227, incorporated herein by reference. In some embodiments, the autonomous machine learning system 201 comprises a random forest 209. In some embodiments, the autonomous machine learning system 201 discovers the associations via operations that include at least a period of unsupervised learning.

Architecture of Cell Culture Apparatus

In some embodiments of the invention, systems and methods of the invention may use cell culture apparatus devices such as those described in U.S. application Ser. No. 16/192,062, U.S. application Ser. No. 16/310,680, U.S. application Ser. No. 15/970,664, U.S. application Ser. No. 15/736,257, International Application No. PCT/US2017/039538, International Application No. PCT/US2016/060701, and International Application No. PCT/US2016/040042, all of which are incorporated herein in their entirety. Such devices may be outfitted with sensors and controllers according to the present invention.

In an embodiment, devices used in the invention may be automated cell culture cartridges and systems for generation of dendritic cells that have uniform, symmetrical flow within the cell culture cartridges. The device may be a completely enclosed, sterile immature DC (iDC) generation system for producing iDCs on a clinical scale, effectively eliminating the need for numerous well plates (or T-flasks/bags), ensuring a sterile and particulate free culture system, and reducing technician time in maintaining cell culture. In an embodiment, the device is an automated cell culture system for aseptically generating therapeutically relevant numbers of iDCs in single cell culture cartridge. The system is also capable of further processing of iDCs to mature them via addition of maturation reagents and stimulation via addition of one or more antigens to the cell culture chamber.

Figure 6:
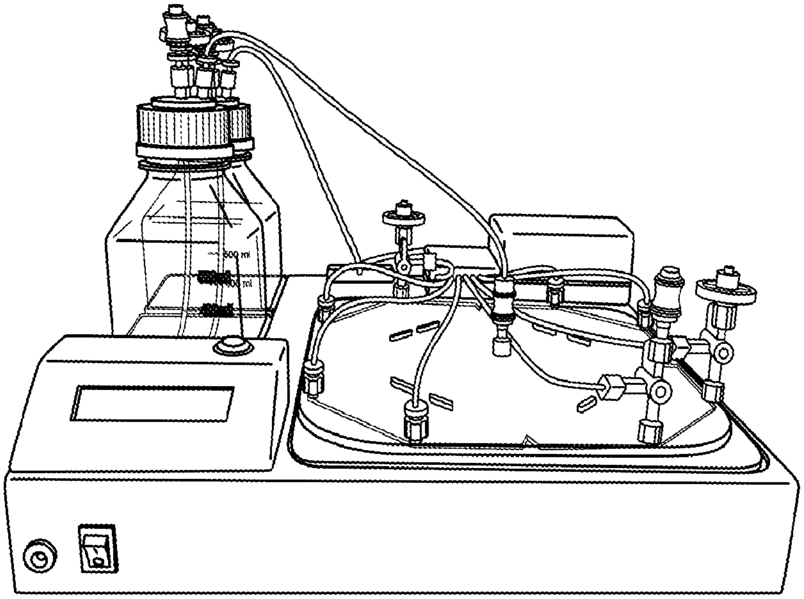
FIG. 6 shows a front view of an embodiment of a cell culture cartridge and system for use in the invention.
Figure 7:
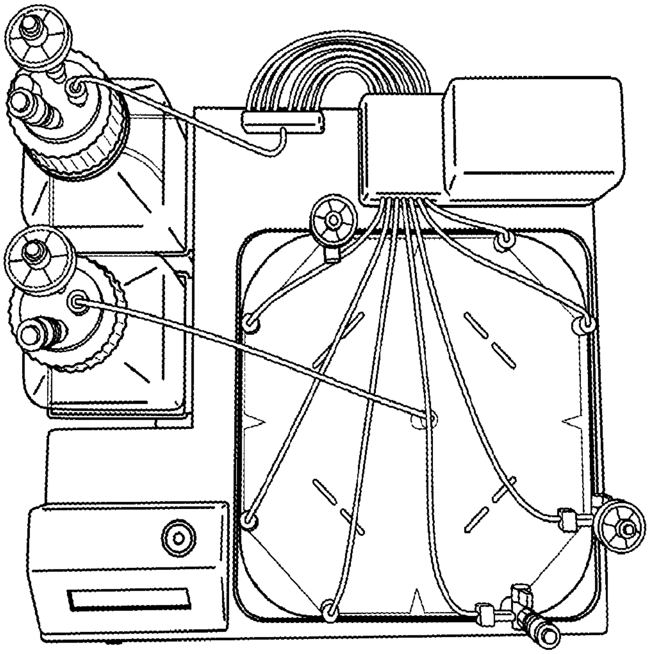
FIG. 7 shows a top view of an embodiment of a cell culture cartridge and system for use in the invention.
Figure 8:
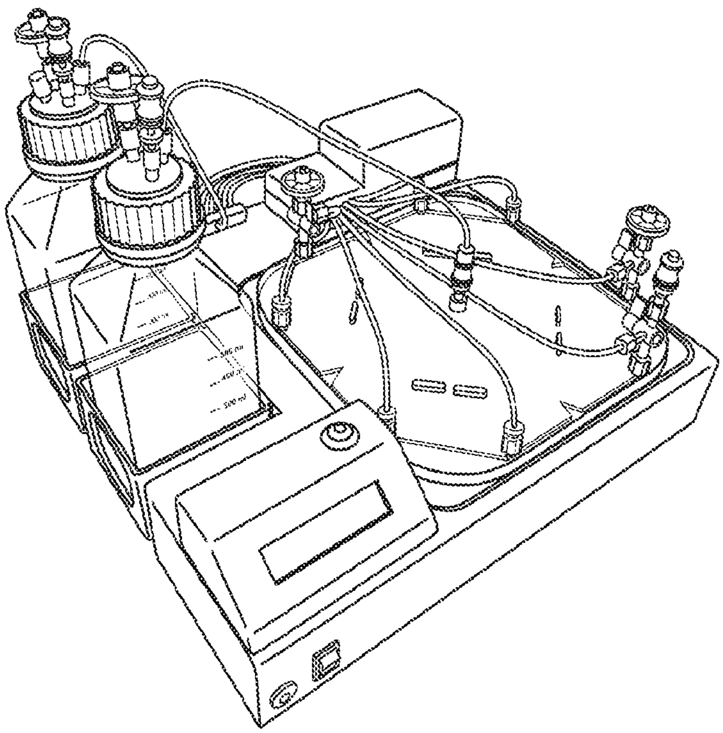
FIG. 8 shows a left side view of an embodiment of a cell culture cartridge and system for use in the invention.
Figure 9:
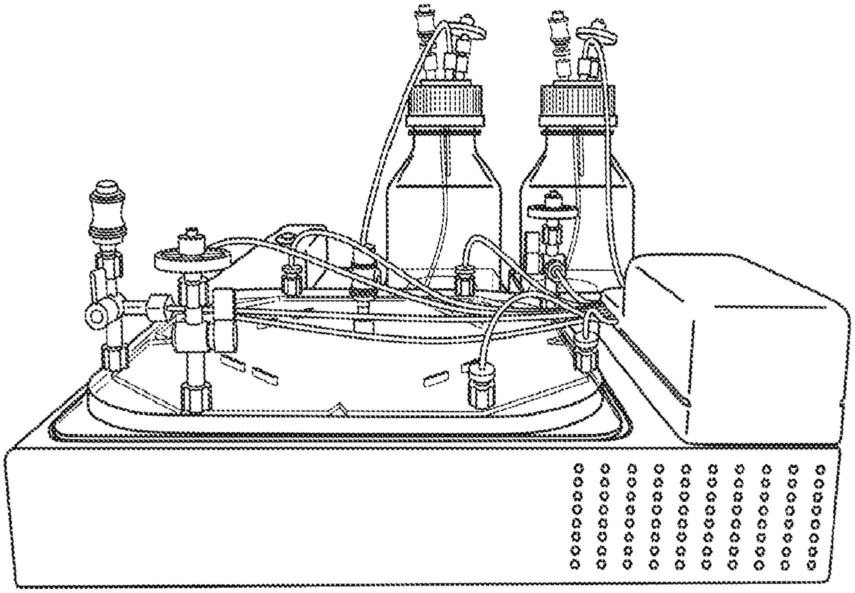
FIG. 9 shows a right side view of an embodiment of a cell culture cartridge and system for use in the invention.

The cell culture system comprises a cell culture cartridge comprising a plurality of zones geometrically configured to provide for symmetrical fluid channels in a cell culture chamber and to avoid dead areas in flow in the cell culture chamber. In some cases, the cartridges for the cell culture apparatus are optically clear or transparent. Such optical clarity, in combination with the fluidic ports being segregated appropriately, allows a user to view cells at any vertical plane within the cartridge. As shown in FIGS. 6-9, embodiments comprise optically clear or transparent cell culture cartridges for use with the invention. FIG. 6 shows a front view of a cell culture cartridge and system for use with the invention. FIG. 7 shows a top view of a cell culture cartridge and system for use with the invention. FIG. 8 shows a left side view of a cell culture cartridge and system for use with the invention. FIG. 9 shows a right side view of a cell culture cartridge and system for use with the invention.

Further, as shown in FIGS. 6-9, stopcocks may be placed on the cartridge or on the reservoir bottles. In particular, stopcocks are placed at specific ports on the cartridge and each serves a specific function. Placement is specific to each function, and work was performed to determine the optimal locations to ensure that the process is successful and workflow is easy. For example, the stopcock at the front is for seeding and harvesting, and the luer activated valve (LAV) on top of stopcock allows for syringe to be sterilely connected. Filters attached to the stopcocks avoid pressure or vacuum buildup within cartridge as liquid is being added or removed from cartridge. In the invention, LAVs may be used on the bottles to add and/or remove medium.

Figure 10:
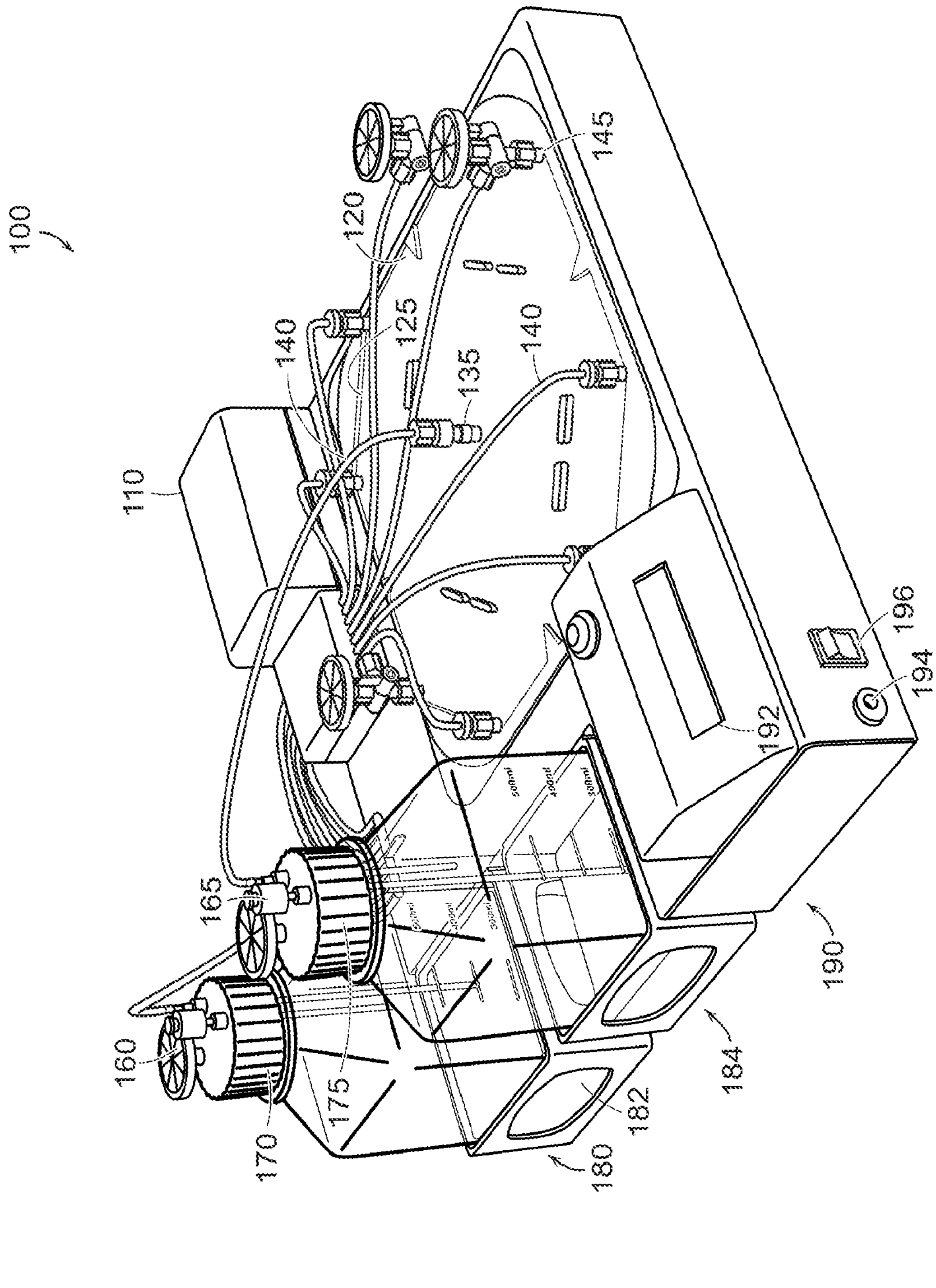
FIG. 10 shows an embodiment of a system for use in the invention.

FIG. 10 shows an embodiment of a system 100 for use with the invention. A peristaltic pump 110 is provided. The pump 110 is used to pump fluid into and out of the cell culture cartridge 120. The cell culture cartridge 120 has a bottom surface 125 to which cells adhere. In other embodiments, cells do not adhere to the bottom surface. The cell culture cartridge 120 has eight fluid inlets 145 arranged at the corners of the cell culture cartridge 120. One fluid outlet 135 is arranged at a center of the cell culture cartridge 120. Connective tubing 140 connects the fluid inlets with the differentiation medium reservoir (perfusion source) 180 containing differentiation medium 182. The differentiation medium reservoir 180 contains differentiation medium 182 that will be pumped into the cell culture cartridge 120. The connective tubing 140 also connects the fluid outlet 135 with the waste reservoir 184. Depleted medium will be pumped out of the cell culture cartridge 120 through the outlet 135 and into the waste reservoir 184. Lids 170 and 175 on the differentiation medium reservoir 180 and the waste reservoir 184 are not removable, thereby maintaining a sterile system. In other embodiments, the lids 170 and 175 are removable. Stopcocks and/or LAVs 160 and 165 on the reservoir bottles 180 and 184 allow for sterile transfer of differentiation medium to fill the inlet bottle and remove waste from the outlet bottle. The console 190 provides designated spaces for arrangement of the previously mentioned components and provides a display/user interface 192, connection 194, and on/off switch 196.

Figure 11:
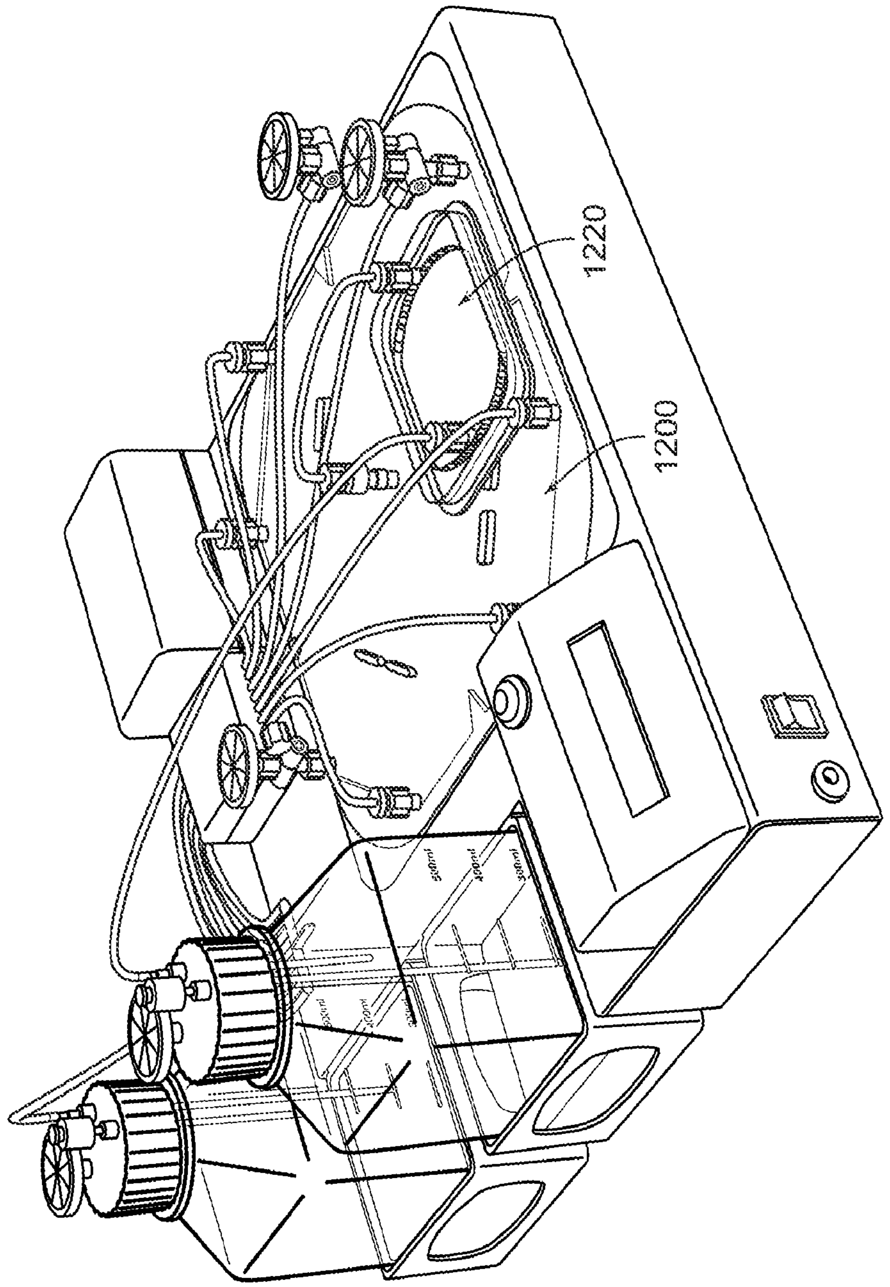
FIG. 11 shows an embodiment of a two cartridge system for use in the invention.

FIG. 11 shows an embodiment of devices with two cartridges for use with the invention. A cell culture cartridge 1200 is provided for monocyte to dendritic cell differentiation. A smaller cartridge 1220 is provided for maturation and antigen pulsing. In other embodiments, maturation and antigen pulsing may be carried out in the main cell culture cartridge without use of a second cartridge.

Figure 12:
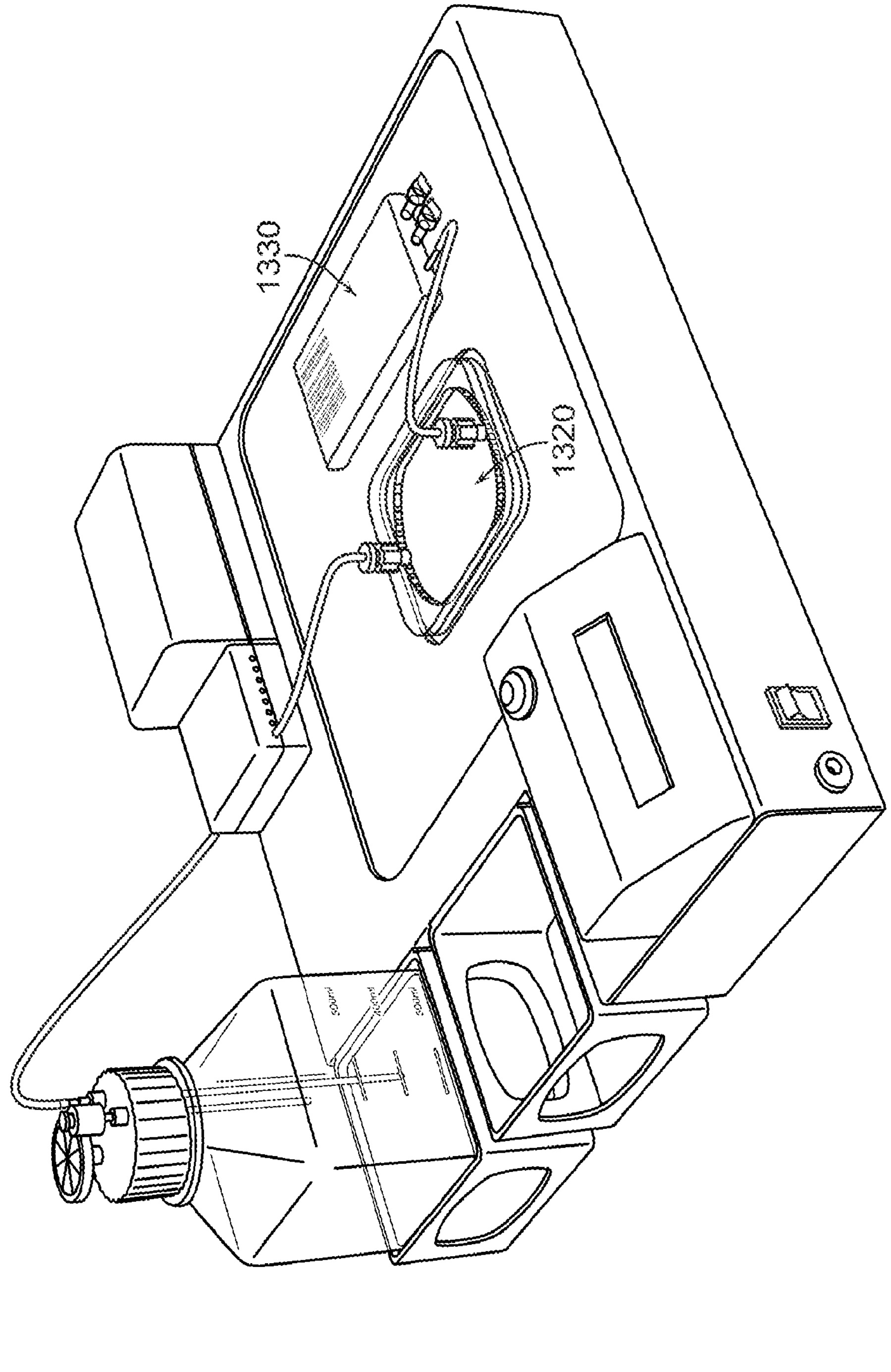
FIG. 12 shows an embodiment showing transfer from a smaller cartridge to an infusion bag for use in the invention.

FIG. 12 shows an embodiment of a device for use with the invention having a smaller cartridge 1320 for maturation and antigen pulsing. The smaller cartridge 1320 is fluidly connected to an infusion bag 1330 containing the final product transferred from the smaller cartridge 1320.

Figure 13:
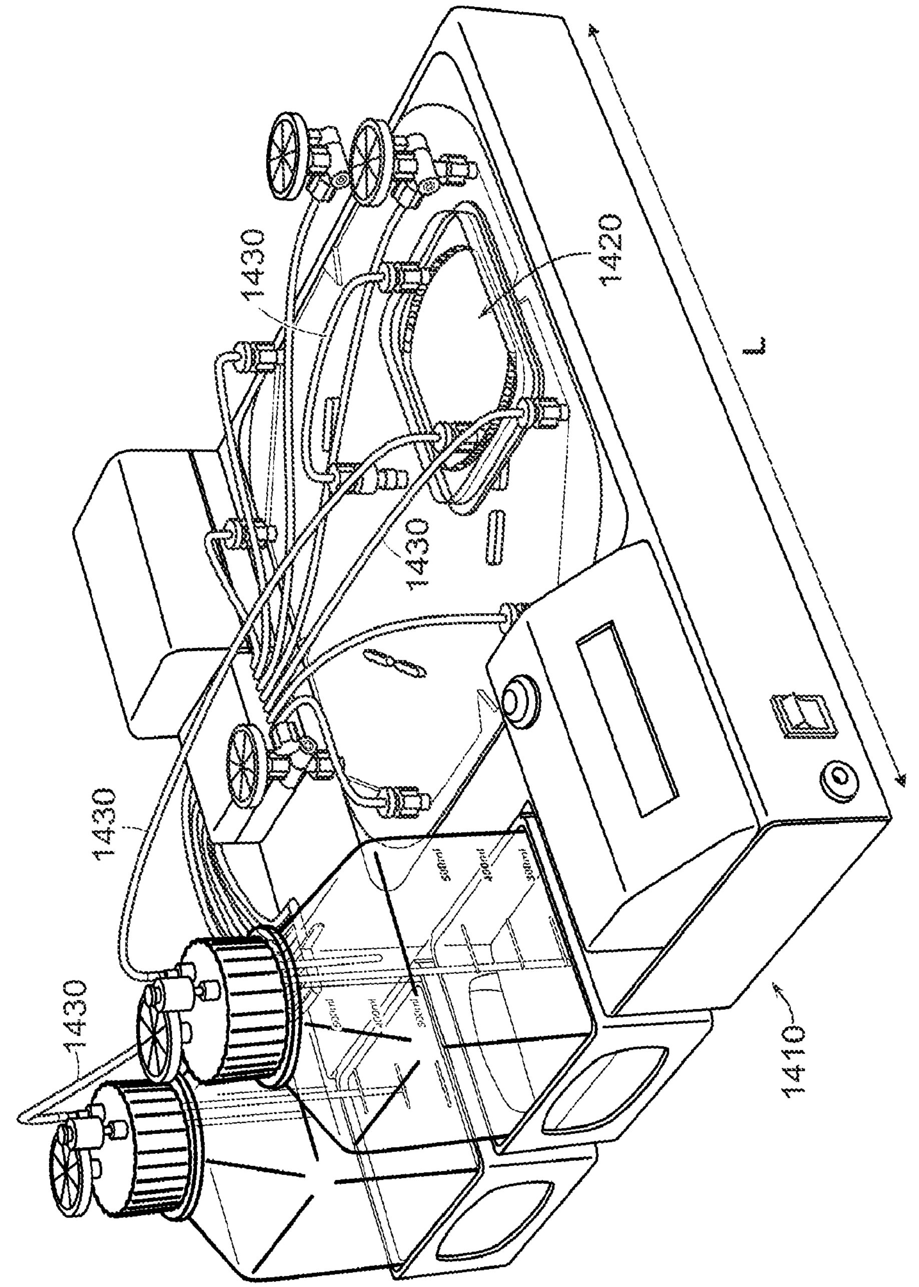
FIG. 13 shows an embodiment of disposable and non-disposable components for use in the invention.

FIG. 13 shows disposable and non-disposable components of devices for use with the invention. The EDEN console 1410 is non-disposable and has a length L. In this embodiment, the length L is 14 inches. A smaller cartridge 1420 is for maturation and antigen pulsing. Connective tubing 1430 connects the inlets and outlet with the reservoirs and the cartridges. The smaller cartridge 1420 and connective tubing 1430 are single-use and disposable.

Figure 14:
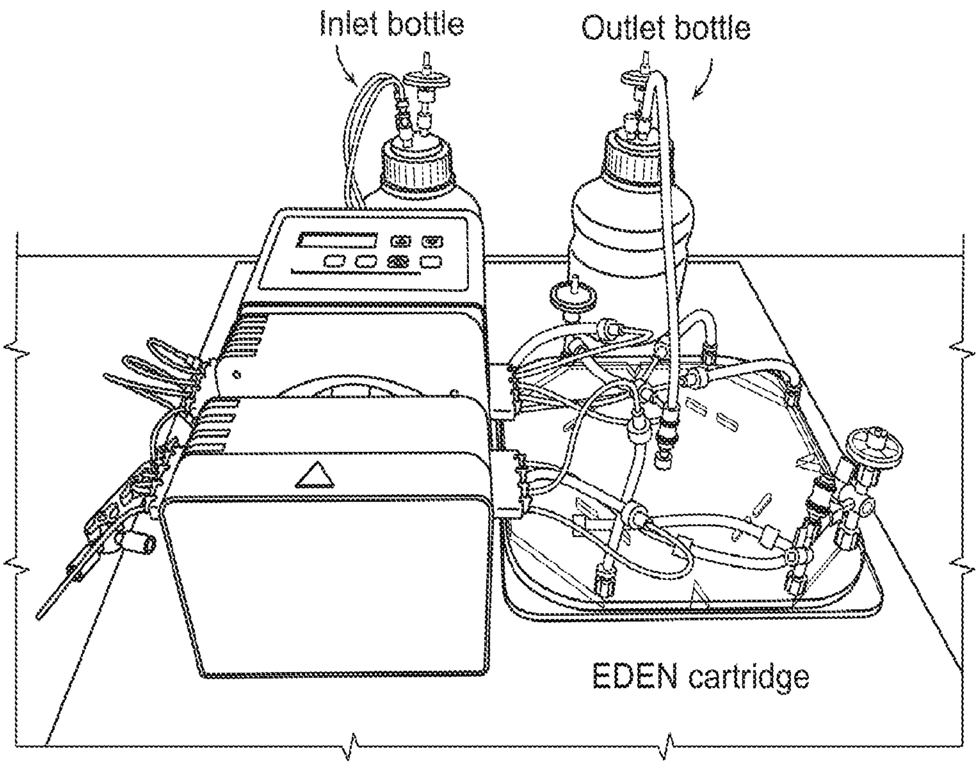
FIG. 14 shows an embodiment of an automated fluidic system for use in the invention.

FIG. 14 shows an embodiment of the EDEN automated fluidic system that may be used with the invention. The EDEN system generates monocyte derived immature dendritic cells (iDCs) while continuously perfusing fresh differentiation medium into the cell culture cartridge. EDEN was developed to generate therapeutically relevant numbers of iDCs in a single cell culture cartridge that is fully enclosed and unopen to the outside environment. Fresh differentiation medium was perfused into the cartridge and depleted medium was removed. EDEN generated iDCs exhibited phenotype expression and iDC yields similar to 6-well plate generated iDCs. iDCs matured in a cartridge according to the invention exhibited standard upregulation of CD80/83/86 and downregulation of CD209.

Figure 15:
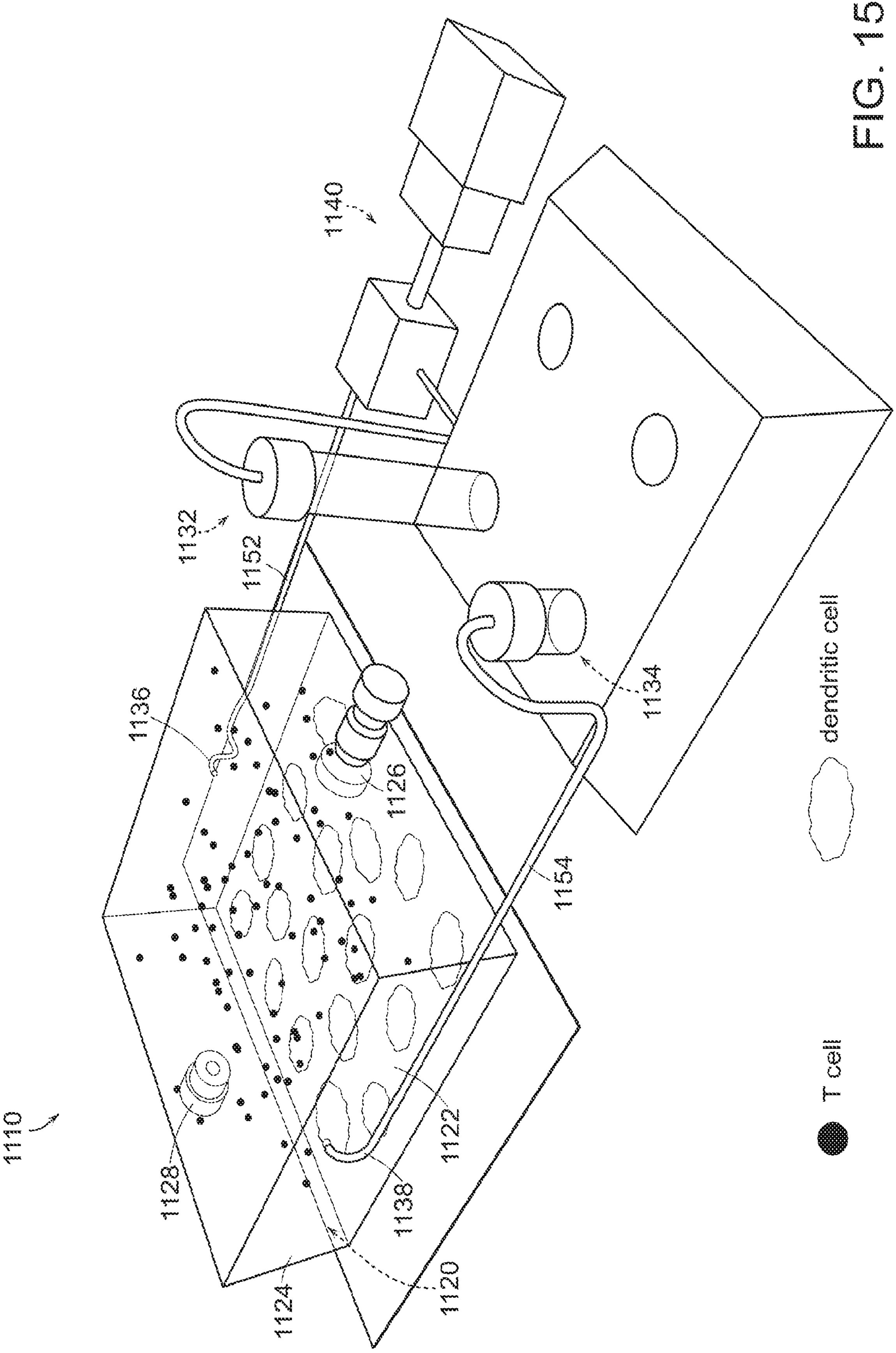
FIG. 15 shows an embodiment of a system with one cell culture chamber for use in the invention.

In some embodiments of the invention, devices such as the biological reactor 1110 shown in FIG. 15 are used. The biological reactor 1110 includes a cell culture chamber 1120 that includes a bottom surface 1122 and at least one additional surface 1124. The bottom surface 1122 is comprised of a first material to which cells adhere, wherein the at least one additional surface 1124 is comprised of a second material that is gas permeable. The cell culture chamber also comprises one or more inlets 1126, 1136 and one or more outlets 1128, 1138. In certain embodiments, the biological reactor also includes at least one perfusion fluid reservoir 1132, at least one waste fluid reservoir 1134, at least one pump 1140 for moving perfusion fluid through the chamber 1120, as well as associated inlets 1136 and outlets 1138 for transporting fluid to and from the reservoirs 1132, 1134 and through the chamber 1120.

With respect to the cell culture chamber 1120, the first material can be any material which is biocompatible and to which antigen-presenting cells (APCs), such as dendritic cells (DCs) will adhere. During the T-cell stimulation and expansion process that occurs in the cell culture chamber 1120, mature APCs will develop and preferably adhere to the bottom surface 1122, whereas the T-cells remain in the supernatant above the bottom surface, making it easier to separately obtain the expanded T-cells.

In one example embodiment, the first material comprises polystyrene. One benefit of using polystyrene for the bottom surface where culture will occur is a useful role that this material plays in the process of generating dendritic cells from PBMCs. Specifically, polystyrene surfaces can be used to enrich monocytes from a heterogeneous suspension of PBMCs. This is a first step in the culture process utilized to generate DCs by differentiation of monocytes via culture in medium containing, for example, IL4 and GM-CSF. The use of the same polystyrene surface for dendritic cell production all the way through one cycle of T-cell stimulation is tremendously valuable from a bioprocess standpoint as it eliminates a large number of transfer steps that would otherwise be necessary, thereby allowing for a closed system for DC-stimulated therapeutic T-cell manufacturing.

In another embodiment, the at least one additional surface 1124 includes a second material that is gas permeable in order to effectuate the gas exchange that is to occur within the cell culture chamber. By fabricating the cell culture chamber such that the bottom surface is made of a material to which cells adhere, such as polystyrene, and the at least one additional surface, such as the side walls and/or the top wall, is made, at least in part, of a gas permeable material, high surface area-gas exchange is achieved in the systems of embodiments of the present invention. Having large surfaces with high permeability, other than the bottom surface, offers the ability to achieve greater levels of gas exchange without having to sacrifice the adherent nature of the bottom surface relative to prior art culture systems, which were limited in the amount of culture medium that could be included and/or lacked a culture-friendly surface to which cells can adhere.

In certain embodiments, the second material includes one or more materials having permeability to oxygen at or greater than a permeability coefficient of 350 and permeability to carbon dioxide at or greater than permeability coefficient of 2000 where the unit of permeability coefficient is [$cm^3$][cm]/[$cm^2$][s][cm Hg]. Example materials include silicone-containing materials such as poly(dimethyl siloxane) (PDMS), which is well known for high oxygen and carbon dioxide permeability (up to three orders of magnitude higher than materials such as polystyrene and PMMA), and polymethylpentene. In one example embodiment, the cell culture chambers comprise polystyrene floors and silicone side and top walls.

In certain aspects, in addition to the second material, the at least one additional surface 1124 can also comprise the first material. For example, and not limitation, the additional surface 1124, such as one or more side walls and/or top wall, can incorporate the second material (e.g., a high permeability polymer, such as a silicone) within a frame made of the first material (e.g., polystyrene). It is also contemplated that the bottom surface can also comprise the second material. However, in some embodiments, the second material is only be intermittently dispersed throughout the bottom surface to ensure that the first material covers a sufficient surface area such that cells can adhere to the surface.

In certain embodiments, the bioreactors 1110 will also include one or more pumps 1140 operably coupled to the cell culture chamber 1120 for perfusing perfusion medium into the cell culture chamber. The bioreactors 1110 can also include one or more fluid reservoirs 1132. The fluid reservoirs 1132 are in fluidic communication with the cell culture chamber 1110 and can be operably coupled to one or more pumps 1140. One or more tubes for connecting the fluid reservoirs to the pumps and cell culture chamber are also provided. In certain aspects, the one or more pumps are configured for pumping fluid from the fluid reservoir, through the cell culture chamber, and into the waste collection reservoir. In the example embodiment shown in FIG. 15, fluid moves from the fluid reservoir 1132, through tubing 1152 to the pump 1140 and into the cell culture chamber 1120 via inlet 1136, back out of the cell culture chamber 1120 via outlet 1138, through tubing 1154, and into the waste collection reservoir 1134.

In certain embodiments, the fluid reservoir and/or waste collection reservoir can each be provided as one or more capped bottles either contained within the cell culture chamber or fluidically coupled to the chamber. Each reservoir contains an inlet port and an outlet port, or an outlet port and a vent fluidically coupled to the inlet of one or more cell culture chambers. In certain aspects, for example, Luer connectors and silicone gaskets cut to fit around the Luer connectors can be used to prevent leakage through either or both of the inlet or outlet.

In certain embodiments, the one or more biological reactors are sized and configured to fit within an incubator, such that the process will be carried out within an incubator. Conditions within the incubator include sustained temperatures of 37° C. and 95-100% humidity. Thus, the materials chosen must have the integrity to withstand these conditions, given that the materials (including fluids and biologics) tend to expand under such conditions.

Furthermore, in some circumstances, conditions within the incubator remain stable, and automated recording of the temperature is possible to have knowledge of temperature fluctuations to correlate with any aberrations in the reactions performed in the incubator. Accordingly, any supply of power should not change the environment within the incubator. For example, certain pumps generate heat. Accordingly, in one embodiment, the pumps are housed separately from the biological reactors, but are still in fluidic and operable communications with the reactors. In another embodiment, the pumps are directly attached to the biological reactors and located within the incubator, but are heat free or are operably connected to a heat sink and/or a fan to dissipate the heat. Regardless of the configuration, the pumps are operably coupled to the biological reactors, and, in turn, the cell culture chambers.

Systems can also include a heater for controlling the temperature of the cell culture reservoir and optionally the fluid reservoir. In such a configuration, no incubator is required, and the system can operate autonomously, with only a source of electrical power. If the system lacks a heater, it can be operated inside of a cell culture incubator.

In other aspects, the cell culture chamber includes one or more sensors (not shown) operably coupled to the cell culture chamber. The sensors may be capable of measuring one or more parameters within the cell culture chamber, such as pH, dissolved oxygen, total biomass, cell diameter, glucose concentration, lactate concentration, and cell metabolite concentration. In embodiments wherein the system includes multiple cell culture chambers, one or more sensors can be coupled to one or more of the cell culture chambers. In certain embodiments, one or more sensors are coupled to one or more cell culture chambers, but not all of the chambers in a system. In other embodiments, one or more sensors are coupled to all of the cell culture chambers in a system. In systems having multiple chambers operably coupled to one or more sensors, the sensors can be the same in each of the chambers to which they are coupled, they can all be different, or some sensors can be the same and some can be different. In certain aspects, the one or more sensors are operably coupled to a computer system (not shown in FIG. 15) having a central processing unit for carrying out instructions, such that automatic monitoring and adjustment of parameters is possible.

Figure 16:
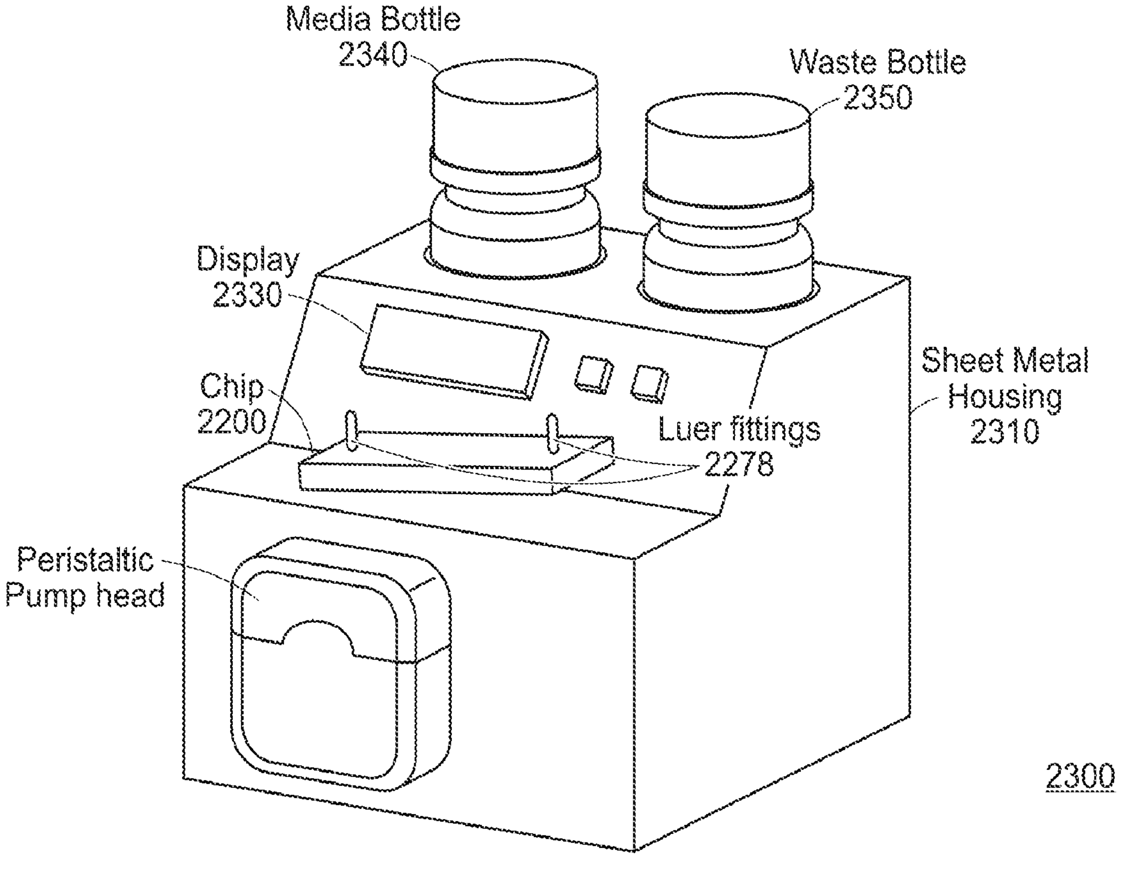
FIG. 16 shows an embodiment of a dendritic cell generation system for use in the invention.

FIG. 16 shows an embodiment of a dendritic cell (DC) generating system 2300 described in International Application No. PCT/US2016/040042, the contents of which are incorporated by reference herein. Such a device may be used with systems and methods of the present invention. The system includes a housing 2310 with spaces for containing a culture medium reservoir 2340 and a waste reservoir 2350 (each the size and shape of commercially available glass or plastic culture medium bottles with plastic caps), a mounting area for a DC differentiation cassette or chip 2200, an exposed peristaltic pump head configured for accepting peristaltic pump tubing leading from the culture medium bottle to the inlet port of the cassette (another tubing leading from the outlet port of the cassette to the waste bottle does not need to pass through the pump head), a display 2330, Luer lock fittings 2278, and control buttons, knobs, or switches. This system can also include a heater (not shown) for controlling the temperature of the cassette and optionally the culture medium reservoir; in such a configuration, no incubator is required, and the system can operate autonomously, with only a source of electrical power. If the system lacks a heater, it can be operated inside of a cell culture incubator. Similar systems that include two or more cassettes and pump heads (e.g., one for each cassette, such as 2, 3, 4, 5, 6, 7 8, 9 10 or more cassettes and pump heads) are also contemplated. In such multi-cassette systems, the control electronics, display, and buttons, knobs, or switches can either be shared among the different cassettes, or duplicated with one set for each cassette.

EXAMPLE 1: PUBLIC DATABASE

In an embodiment, systems and methods of the invention pull data from a public database for use in determining the cell culture protocol. Any suitable public database comprises data for one or more cell culture protocols and systems of the invention may connect to the database in order to receive the cell culture protocol data. For example, the invention may pull data from the Cell-culture Database described in Amirkia and Qiubao, Cell-culture Database: Literature-based reference tool for human and mammalian experimentally based cell culture applications; Bioinformation, 2012; 8(5): 237-238, incorporated herein in its entirety by reference. The Cell-culture Database is publicly available at cell-lines.toku-e.com and is helpful for choosing the most effective media, supplements, and antibiotics for cells, determining concentrations and combinations of antibiotics for selection and transfection experiments, and locating literature relevant to cell lines of interest or plasmids or vectors of interest. To use the Cell-culture Database, the name of a cell line, plasmid, or vector is entered in a search box and relevant data is browsed. The database provides information about other experiments which have used the same cell lines or plasmid, such as what other media has been used to grow the cells in question.

In such an embodiment, a controller operably associated with a cell culture apparatus receives initial data associated with cells to be cultured. For example, the user or lab technician inputs data on the cell line. The controller then connects to the publicly available database, such as the Cell-culture Database. The Cell-culture Database provides a variety of information about cell culture protocols when relevant input data is provided. The controller provides the data on the cell line as an "input" in the Cell-culture Database. Methods of the invention include browsing the results obtained from such input, such as media used for growing the cells, and using the results to determine a cell culture protocol.

In some cases, the determined cell culture protocol comprises a protocol pulled directly from the public database. In some cases, the determined cell culture protocol may be instantly used for cell culture. The determined cell culture protocol may also be stored for future use, such as being stored in an internal database.

EXAMPLE 2: INTERNAL DATABASE

In an embodiment, systems and methods of the invention pull data from an internal database for use in determining the cell culture protocol. An internal database may include information on cell culture protocols previously used in the lab setting. For instance, the database may include information obtained from cell apparatus settings and information from lab notebooks. Information in the internal database may include any relevant information on cell culture protocols, such as cell type, media type, pH, temperature, duration of culture steps, and fluid flow rate use during culture.

In such an embodiment, a controller operably associated with a cell culture apparatus receives data associated with cells to be cultured. For example, the user or lab technician inputs data regarding the cell line. The controller then connects to the internal database, such as a database documenting all prior cell culture protocols used in the lab. Based on the input, the database provides information related to past cell culture protocols used for that cell type. For example, information may include type of media, pH, temperature, duration of steps, and fluid flow rate use during culture. Methods of the invention include browsing the results obtained from such input, such as media used for growing the cells, and using the results to determine a cell culture protocol.

In some cases, the determined cell culture protocol comprises a protocol pulled directly from the internal database. In some cases, the determined cell culture protocol may be instantly used for cell culture. The determined cell culture protocol may also be stored for future use, such as being stored in the internal database.

EXAMPLE 3: COMBINATION OF DATABASES

In an embodiment, systems and methods of the invention pull data from a combination of databases for use in determining the cell culture protocol. The databases may be any suitable database comprising one or more cell culture protocols. For example, the databases may be a combination of publicly available databases. In another example, the databases may be a combination of publicly available databases and an internal database.

In such an example, a controller operably associated with a cell culture apparatus receives data associated with cells to be cultured. The controller then connects to a first database, such as a public database, to receive cell culture protocol data. The controller connects to another database, such as an internal database, to receive cell culture protocol data. The controller then determines a cell culture protocol for the cells to be cultured based on the data obtained from the public database and internal database.

In some cases, the determined cell culture protocol comprises a protocol pulled directly from the internal database and modified based on the data from the public database. In some cases, the determined cell culture protocol comprises a protocol pulled directly from the public database and modified based on the data from the internal database. In some cases, the determined cell culture protocol comprises a protocol pulled directly from a first public database and modified based on data from a second public database. In some cases, the determined cell culture protocol may be instantly used for cell culture. The determined cell culture protocol may also be stored for future use, such as being stored in an internal database.

EXAMPLE 4: DATABASE AND FEEDBACK

In an embodiment, systems and methods of the invention pull data from one or more databases and also include feedback data from sensors for use in determining the cell culture protocol. Feedback data includes data from a plurality of sensors monitoring conditions of the cell culture procedure.

In such an example, a controller operably associated with a cell culture apparatus receives data associated with cells to be cultured, such as the cell type. The controller then connects to a database, which may be any suitable public or internal database comprising one or more cell culture protocols. The controller receives cell culture protocol data from the database. The controller receives data from the plurality of sensors on the cell culture apparatus, such as temperature, pressure, pH, temperature, and fluid flow rate. The data obtained from the sensors is used to modify the cell culture protocol obtained from the database, thereby determining a cell culture protocol based on the data obtained from the database and feedback data. The determined cell culture protocol may be instantly used for cell culture. The determined cell culture protocol may also be stored for future use, such as in an internal database.

EXAMPLE 5: OPTIMIZATION OF USER-DEFINED PARAMETERS

In an embodiment, systems and methods of the invention may be used to optimize a cell culture procedure based on user-defined parameters. In some cases, the user-defined parameters are selected from pH, turbidity (reflecting cell proliferation), glucose, lactate, or any other measure of cell health or identity. A user would input a desired parameter and load the system with cells and base medium. Methods of the invention are then used to self-optimize the cell culture procedure in the system in order to maintain the user-defined set of parameters. In such an example, methods and systems of the invention sense the level of the parameter or parameters of interest at least once during the cell culture process. Optionally, the parameter of interest may be sensed multiple times throughout the cell culture process.

The invention then optimizes the user-defined parameters by deciding whether to change culture conditions. For example, systems and methods of the invention include making a decision on whether or not to change culture conditions based on the sensed parameter levels. In certain situations, information on optimization of parameters may not be retrievable from a database, such as when a new experiment or protocol is being carried out for the first time. In certain cases, systems and methods of the invention then change the culture conditions based on the decision. In some cases, systems and methods of the invention manipulate the flow rate to change glucose concentration or lactate concentration. In some cases, systems and methods of the invention add supplements, such as cytokines, growth factors, and serum, from reservoirs. The reservoirs may be included in the system (or on-board) or may be outside of the incubator, connected via pumps to the culture vessel. Following the end of the cell culture procedure, methods and systems of the invention store the optimized protocol in a database, such as an internal database, to serve as a reference for future use.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

While the present invention has been described in conjunction with certain embodiments, one of ordinary skill, after reading the foregoing specification, will be able to effect various changes, substitutions of equivalents, and other alterations to the compositions and methods set forth herein.

The invention claimed is:

1. A system for dynamically optimizing a cell culture protocol, the system comprising:

a cell culture apparatus configured to communicate with one or more databases containing cell culture protocol data, the cell culture apparatus comprising:

a cell culture cartridge comprising a top surface, a bottom surface, an outlet positioned at a center of the top surface, and a plurality of corners with an inlet positioned at each one of the plurality of corners, wherein the bottom surface and the top surface together, at least in part, define a plurality of zones comprising one of the corners and one of the inlets such that the zones converge at the center of the top surface, wherein each of the plurality of zones, due at least in part to the position of the inlet in each zone relative to the outlet provide for symmetrical fluid flow between its respective inlet and the outlet to avoid dead areas in flow within each of the plurality of zones;

a controller, one or more sensors communicatively coupled to the controller and configured to measure one or more cell culture conditions, and an interface with which one or more users can interact, via associated computing devices, for dynamically optimizing a cell culture protocol, wherein the controller comprises a hardware processor coupled to memory containing instructions executable by the processor to cause the controller to:

receive, from the one or more users, data associated with desired cells to be cultured as a first data;

communicate with the one or more databases to retrieve cell culture protocol data relevant to the desired cells as a second data input;

analyze the first data input and the second data input using a machine learning system comprising a deep learning neural network comprising an input layer, a plurality of hidden layers, and an output layer, wherein the machine learning system is configured to normalize and categorize the first data input and the second data input to generate a plurality of feature vectors and to determine statistically significant associations between the first data input and the second data input to thereby generate an optimized cell culture protocol tailored to the cells to be cultured, wherein the optimized cell culture protocol comprises one or more specific cell culture conditions;

receive, as a third data input, real-time sensor feedback from the one or more sensors during cell culture; and dynamically adjust the cell culture protocol during cell culture based on the sensor feedback to thereby maintain optimized specific cell culture conditions.

2. The system of claim 1, wherein the controller is integrated.

3. The system of claim 1, wherein the controller is distributed.

4. The system of claim 1, wherein the cell culture apparatus is a single-use cell culture apparatus.

5. The system of claim 1, wherein the one or more sensors are single-use sensors.

6. The system of claim 1, wherein the feedback is associated with a cell culture condition comprising at least one of pH, glucose concentration, lactate concentration, dissolved oxygen, total biomass, cell diameter, temperature, cell type, media type, and fluid flow rate.

7. The system of claim 1, wherein the one or more databases is a database comprising one or more cell culture protocols previously developed by the system.

8. The system of claim 1, wherein the one or more databases is a publicly available database comprising one or more cell culture protocols.

9. The system of claim 1, wherein the system is configured to receive at least one set level of a user-defined parameter, wherein the specific cell culture conditions are optimized to maintain the set level of the user defined parameter.

10. The system of claim 9, wherein the user-defined parameter comprises at least one of pH, turbidity, glucose concentration, lactate concentration, a measure of cell health, a measure of cell identity, or a combination thereof.

11. A method of dynamically optimizing a cell culture protocol comprising:

providing a cell culture apparatus configured to communicate with one or more databases containing cell culture protocol data, wherein the cell culture apparatus comprises a cell culture cartridge comprising a top surface, a bottom surface, an outlet positioned at a center of the top surface, and a plurality of corners with an inlet positioned at each one of the plurality of corners, wherein the bottom surface and the top surface together, at least in part, define a plurality of zones comprising one of the corners and one of the inlets such that the zones converge at the center of the top surface, wherein each of the plurality of zones, due at least in part to the position of the inlet in each zone relative to the outlet provide for symmetrical fluid flow between its respective inlet and the outlet to avoid dead areas in flow within each of the plurality of zones, a controller, one or more sensors communicatively coupled to the controller and configured to measure one or more cell culture conditions, and an interface with which one or more users can interact, via associated computing devices, for dynamically optimizing a cell culture protocol;

receiving from the one or more users, data associated with desired cells to be cultured as a first input;

communicating with the one or more databases to retrieve cell culture protocols data relevant to the desired cells as a second data input;

analyzing the first data input and the second data input using a machine learning system comprising a deep learning neural network comprising an input layer, a plurality of hidden layers, and an output layer, wherein the machine learning system is configured to normalize and categorize the first data input and the second data input to generate a plurality of feature vectors and to determine statistically significant associations between the first data input and the second data input to thereby generate an optimized cell culture protocol tailored to the cells to be cultured, wherein the optimized cell culture protocol comprises one or more specific cell culture conditions;

receiving, as a third data input, real-time sensor feedback from the one or more sensors during cell culture; and dynamically adjusting the cell culture protocol during cell culture based on the sensor feedback to thereby maintain optimized specific cell culture conditions.

12. The method of claim 11, wherein the feedback is associated with a cell culture condition comprising at least one of pH, glucose concentration, lactate concentration, dissolved oxygen, total biomass, cell diameter, temperature, cell type, media type, and fluid flow rate.

13. The method of claim 11, wherein the one or more databases is a database comprising one or more cell culture protocols previously developed by a system for monitoring and controlling cell culture and a publicly available database comprising one or more cell culture protocols.

14. The method of claim 11, further comprising reporting the optimized cell culture protocol.

15. The method of claim 14, wherein reporting comprises providing an alert when a level falls outside specified ranges.

16. The method of claim 15, wherein the alert comprises an email alert, voice alert, text alert, or combination thereof.

17. The method of claim 15, wherein a level comprises a pH level, dissolved oxygen level, total biomass level, cell diameter level, or temperature level.

18. The method of claim 14, wherein reporting further comprises providing monitoring information to a user.

19. The method of claim 18, wherein monitoring information comprises profiles of pH, dissolved oxygen, total biomass, cell diameter, and temperature.

20. The method of claim 11, wherein determining the cell culture protocol further comprises deciding to terminate the culture process, to stop using further reagents, to alert the user, or to shut the system down.

21. The method of claim 11, wherein the method further comprises receiving a set level of a user-defined parameter, wherein dynamically adjusting the cell culture protocol comprises optimizing the specific cell culture conditions to maintain the set level of the user-defined parameter.

22. The method of claim 21, wherein the user-defined parameter comprises at least one of pH, turbidity, glucose concentration, lactate concentration, a measure of cell health, a measure of cell identity, or a combination thereof.

* * * * *